(12) United States Patent
Sinha et al.

(10) Patent No.: US 11,830,624 B2
(45) Date of Patent: Nov. 28, 2023

(54) SYSTEM AND METHOD FOR DETERMINING DATA QUALITY FOR CARDIOVASCULAR PARAMETER DETERMINATION

(71) Applicant: Riva Health, Inc., Burlingame, CA (US)

(72) Inventors: Tuhin Sinha, Burlingame, CA (US); Mark Mozolewski, Burlingame, CA (US)

(73) Assignee: Riva Health, Inc., Burlingame, CA (US)

( * ) Notice: Subject to any disclaimer, the term of this patent is extended or adjusted under 35 U.S.C. 154(b) by 0 days.

(21) Appl. No.: 17/939,773

(22) Filed: Sep. 7, 2022

(65) Prior Publication Data

US 2023/0074082 A1 Mar. 9, 2023

Related U.S. Application Data

(60) Provisional application No. 63/241,436, filed on Sep. 7, 2021.

(51) Int. Cl.
*G06K 9/00* (2022.01)
*G16H 50/20* (2018.01)
(Continued)

(52) U.S. Cl.
CPC ......... *G16H 50/20* (2018.01); *A61B 5/02108* (2013.01); *A61B 5/02416* (2013.01);
(Continued)

(58) Field of Classification Search
None
See application file for complete search history.

(56) References Cited

U.S. PATENT DOCUMENTS

| 5,649,543 A | 7/1997 | Hosaka et al. |
|---|---|---|
| 6,337,629 B1 | 1/2002 | Bader |

(Continued)

FOREIGN PATENT DOCUMENTS

| CN | 103826532 A | 5/2014 |
|---|---|---|
| CN | 104337509 A | 2/2015 |

(Continued)

OTHER PUBLICATIONS

Elgendi, Mohamed, "Merging digital medicine and economics: Two moving averages unlock biosignals for better health", Diseases 6.1 (2018): 6. (Year: 2018).

(Continued)

*Primary Examiner* — Wei Wen Yang
(74) *Attorney, Agent, or Firm* — Jeffrey Schox; Diana Lin

(57) ABSTRACT

The system for cardiovascular parameter data quality determination can include a user device and a computing system, wherein the user device can include one or more sensors, the computing system, and/or any suitable components. The computing system can optionally include a data quality module, a cardiovascular parameter module, a storage module, and/or any suitable modules. The method for cardiovascular parameter data quality determination can include acquiring data and determining a quality of the data. The method can optionally include processing the data, and/or determining a cardiovascular parameter, training a data quality module, any suitable steps.

19 Claims, 24 Drawing Sheets

(51) Int. Cl.
*G16H 30/20* (2018.01)
*A61B 5/00* (2006.01)
*A61B 5/024* (2006.01)
*A61B 5/021* (2006.01)
*G06T 7/00* (2017.01)

(52) U.S. Cl.
CPC .......... *A61B 5/6843* (2013.01); *A61B 5/721* (2013.01); *A61B 5/7221* (2013.01); *A61B 5/7264* (2013.01); *G16H 30/20* (2018.01); *A61B 2576/00* (2013.01); *G06T 7/0012* (2013.01); *G06T 2207/20081* (2013.01); *G06T 2207/30048* (2013.01)

(56) References Cited

U.S. PATENT DOCUMENTS

| | | | |
|---|---|---|---|
| 6,475,153 | B1 | 11/2002 | Khair et al. |
| 6,993,377 | B2 | 1/2006 | Flick et al. |
| 7,286,875 | B1 | 10/2007 | Park et al. |
| 7,787,946 | B2 | 8/2010 | Stahmann et al. |
| 8,239,010 | B2 | 8/2012 | Banet et al. |
| 8,761,853 | B2 | 6/2014 | Thaveeprungsriporn et al. |
| 9,665,213 | B2 | 5/2017 | Christman et al. |
| 10,420,515 | B2 | 9/2019 | Sinha et al. |
| 2003/0163057 | A1 | 8/2003 | Flick et al. |
| 2008/0045818 | A1 | 2/2008 | Wood et al. |
| 2009/0326386 | A1 | 12/2009 | Sethi et al. |
| 2010/0168589 | A1 | 7/2010 | Banet et al. |
| 2011/0066051 | A1 | 3/2011 | Moon et al. |
| 2011/0077531 | A1 | 3/2011 | Addison et al. |
| 2011/0224564 | A1 | 9/2011 | Moon et al. |
| 2012/0029320 | A1 | 2/2012 | Watson et al. |
| 2012/0179011 | A1 | 7/2012 | Moon et al. |
| 2012/0190947 | A1 | 7/2012 | Chon et al. |
| 2013/0276785 | A1 | 10/2013 | Melker et al. |
| 2013/0310656 | A1 | 11/2013 | Lim et al. |
| 2013/0345568 | A1 | 12/2013 | Mestha et al. |
| 2014/0003454 | A1 | 1/2014 | Kaemmerer et al. |
| 2014/0275854 | A1 | 9/2014 | Venkatraman et al. |
| 2014/0278220 | A1 | 9/2014 | Yuen |
| 2014/0303454 | A1 | 10/2014 | Clifton et al. |
| 2015/0037937 | A1 | 2/2015 | Park et al. |
| 2015/0080746 | A1 | 3/2015 | Bleich et al. |
| 2015/0182132 | A1 | 7/2015 | Harris et al. |
| 2015/0313484 | A1 | 11/2015 | Burg et al. |
| 2015/0324977 | A1 | 11/2015 | Magrath et al. |
| 2015/0379370 | A1 | 12/2015 | Clifton et al. |
| 2016/0058375 | A1 | 3/2016 | Rothkopf |
| 2016/0256117 | A1 | 9/2016 | Baik et al. |
| 2016/0287110 | A1* | 10/2016 | Morris .................. A61B 5/024 |
| 2016/0302674 | A1 | 10/2016 | Moyer et al. |
| 2016/0360980 | A1 | 12/2016 | Sinha et al. |
| 2017/0007137 | A1 | 1/2017 | Hong et al. |
| 2017/0071516 | A1 | 3/2017 | Bhagat et al. |
| 2017/0079533 | A1 | 3/2017 | Robinson et al. |
| 2018/0146865 | A1 | 5/2018 | Ortlepp |
| 2018/0184983 | A1 | 7/2018 | Petersen et al. |
| 2019/0059753 | A1 | 2/2019 | Chen et al. |
| 2019/0175120 | A1 | 6/2019 | Huang |
| 2019/0357855 | A1* | 11/2019 | Sinha .................. A61B 5/7275 |
| 2021/0212582 | A1 | 7/2021 | Fathieh et al. |
| 2022/0133158 | A1 | 5/2022 | Jones et al. |
| 2022/0133162 | A1 | 5/2022 | Jones et al. |
| 2022/0133241 | A1* | 5/2022 | Jones ........................ G06T 7/90 600/485 |

FOREIGN PATENT DOCUMENTS

| | | |
|---|---|---|
| EP | 2992820 A2 | 3/2016 |
| KR | 20160028093 A | 3/2016 |
| WO | 2014022906 A1 | 2/2014 |
| WO | 2015193551 A1 | 12/2015 |
| WO | 2017152098 A1 | 9/2017 |

OTHER PUBLICATIONS

Lee, Han-Wook , et al., "he periodic moving average filter for removing motion artifacts from PPG signals", International Journal ofControl, Automation, and Systems 5.6 (2007): 701-706. (Year: 2007).

Perpetuini, David , et al., "Multi-site photoplethysmographic and electrocardiographic system for arterial stiffness and cardiovascular status assessment", Sensors 19.24 (2019): 5570. (Year: 2019).

Rojano, Juan F., "Singular value decomposition of the time-frequency distribution of PPG signals for motion artifact reduction", Int. J. Signal Process. Syst 4.6 (2016): 475-482. (Year: 2016).

Scholze, A., et al. , "Increased arterial vascular tone during the night in patients with essential hypertension", Journal of Human Hypertension (2007) 21, 60-67. published online Oct. 5. [retrieved on Aug. 22, 2016] retrieved from the Internet : http://www.nature.com.

Sugita, Norihiro , et al., "Techniques for estimating blood pressure variation using video images", 37th Annual International Conference of the IEEE Engineering in Medicine and Biology Society (EMBC) Aug. 29, 2015.

Vadrevu, Simhadri , et al., "A robust pulse onset and peak detection method for automated PPG signal analysis system", IEEE Transactions on Instrumentation and Measurement 68.3 (2018): 807-817. (Year: 2018).

Wang, Lu , et al., "Multi-Gaussian fitting for pulse waveform using weighted least squares and multi-criteria decision making method", Computers in biology and medicine 43.11 (2013): 1661-1672. (Year: 2013).

* cited by examiner

*Software as a Medical Device (SaMD)*

*Example of red and blue chromas, plotted over time* live video preview of finger approaching image sensor lens live video preview of finger fully covering image sensor lens

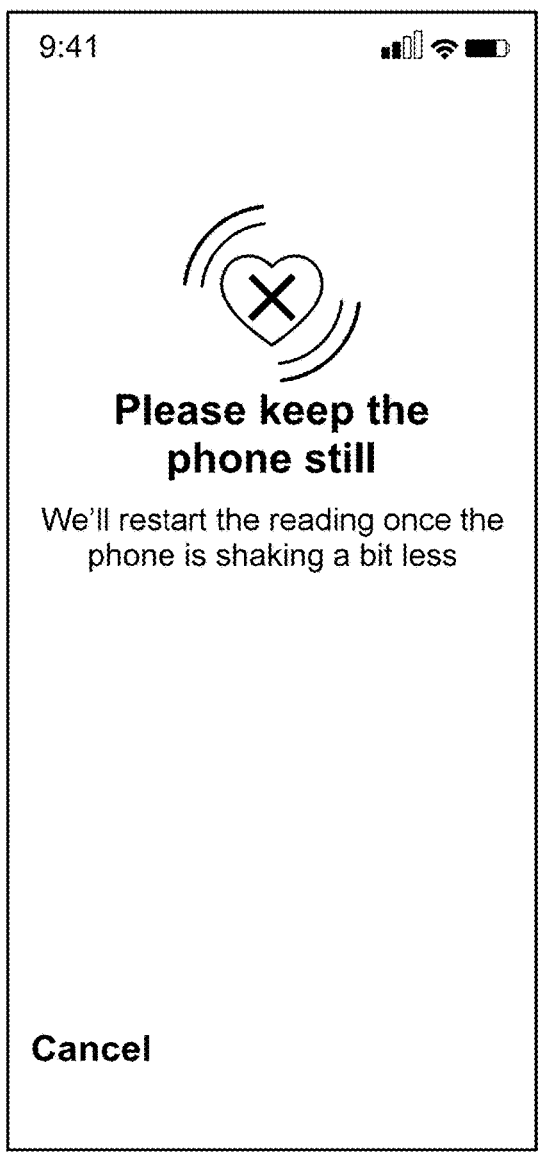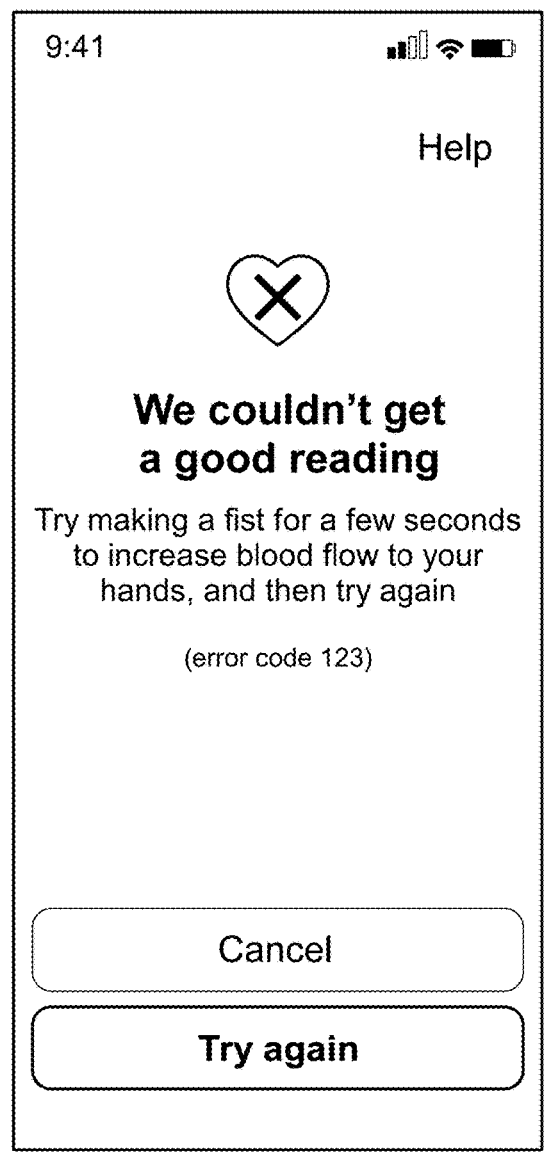
unacceptable motion
unacceptable body region contact and/or placement
FIGURE 17A
FIGURE 17B

SYSTEM AND METHOD FOR DETERMINING DATA QUALITY FOR CARDIOVASCULAR PARAMETER DETERMINATION

CROSS-REFERENCE TO RELATED APPLICATIONS

This application claims the benefit of U.S. Provisional Application No. 63/241,436 filed 7 Sep. 2021, which is incorporated in its entirety by this reference.

TECHNICAL FIELD

This invention relates generally to the cardiovascular parameter field, and more specifically to a new and useful system and method in the cardiovascular parameter field.

BRIEF DESCRIPTION OF THE FIGURES

FIG. 17A depicts an illustrative example of guiding a user based on a motion parameter.

FIG. 17B depicts an illustrative example of guiding a user based on a contact parameter and/or a placement parameter.

DETAILED DESCRIPTION

The following description of the embodiments of the invention is not intended to limit the invention to these embodiments, but rather to enable any person skilled in the art to make and use this invention.

1. Overview

Figure 1A:
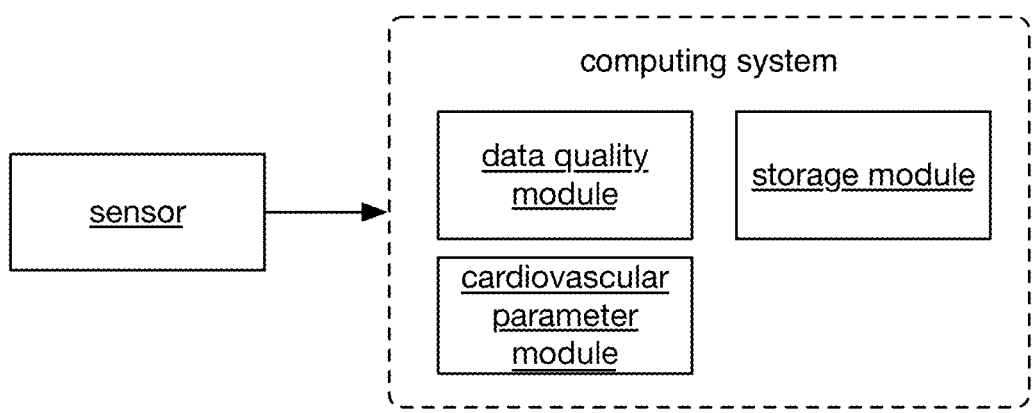
FIG. 1A is a schematic representation of a variant of the system.

As shown in FIG. 1A, the system can include a user device and a computing system. The user device can include one or more sensors, the computing system, and/or any suitable components. The computing system can include a data quality module, a cardiovascular parameter module, a storage module, and/or any suitable module(s).

Figure 2:
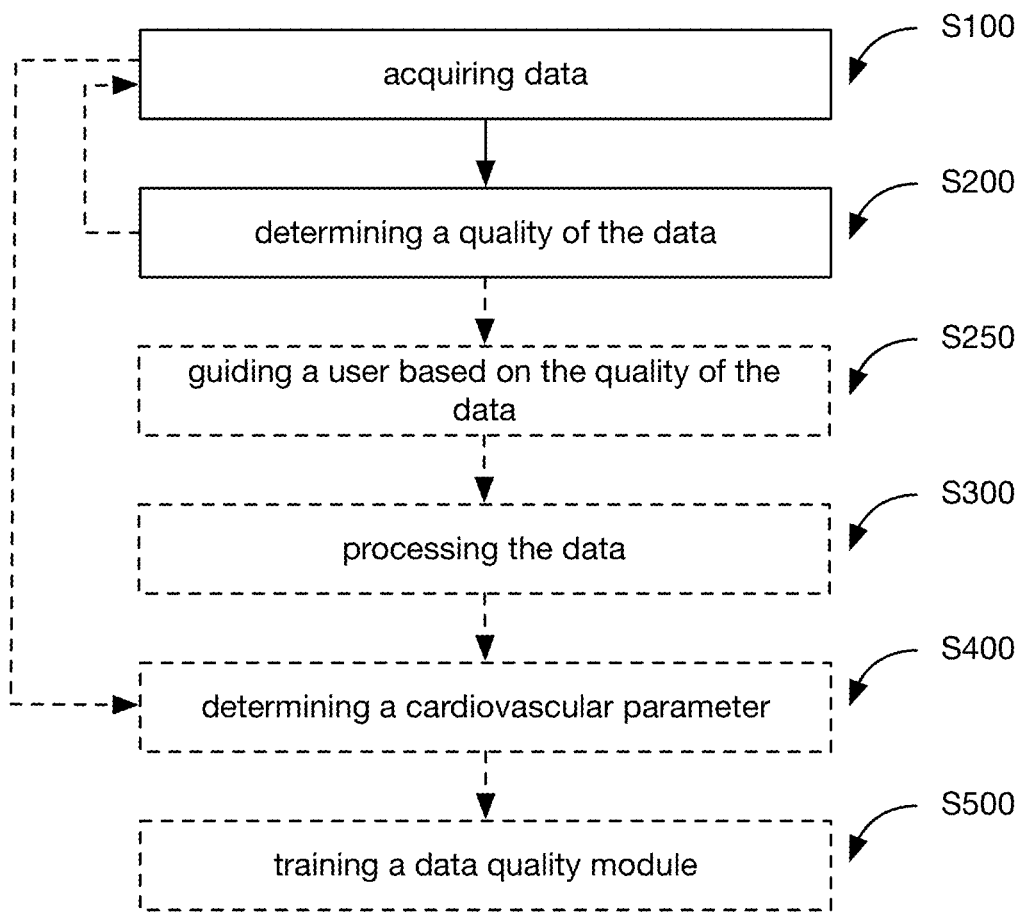
FIG. 2 is a schematic representation of a variant of the method.

As shown in FIG. 2, the method can include acquiring data S100 and determining a quality of the data S200. The method can optionally include guiding a user based on the quality of the data S250, processing the data S300, determining a cardiovascular parameter S400, training a data quality module S500, and/or any suitable steps.

The system and method preferably function to determine a quality associated with plethysmogram data and/or determine a cardiovascular parameter based on the plethysmogram data. However, the system and method can otherwise function. Exemplary cardiovascular parameters include: blood pressure, arterial stiffness, stroke volume, heart rate, blood volume, pulse transit time, phase of constriction, pulse wave velocity, heart rate variability, blood pressure variability, medication interactions (e.g., impact of vasodilators, vasoconstrictors, etc.), cardiovascular drift, cardiac events (e.g., blood clots, strokes, heart attacks, etc.), cardiac output, cardiac index, systemic vascular resistance, oxygen delivery, oxygen consumption, baroreflex sensitivity, stress, sympathetic/parasympathetic tone, respiratory rate, blood vessel viscosity, venous function, ankle pressure, genital response, venous reflux, temperature sensitivity, and/or any suitable cardiovascular parameters and/or properties.

2. Examples

In an example, the system can include: a user device that includes a local computing system, a camera, a torch (e.g., flash), and a motion sensor; and a remote computing system (e.g., remote from the user device). The local computing system can include a data quality module, wherein the data quality module includes a motion model, a body region contact model, and a placement model. A cardiovascular parameter module is preferably executed by the remote computing system, but can be distributed between the local and remote computing systems and/or located on the local computing system. In this example, the method can include: a user placing their finger on the torch and a lens of the camera, acquiring a video segment via the camera and a first motion dataset via the motion sensor, extracting a set of image attributes from the video segment (e.g., attributes of the image itself, instead of attributes of a scene captured by the image), and determining a data quality associated with the video segment based on the set of image attributes and the first motion dataset. Specific examples of image attributes include: total luminance (e.g., sum of luminance across all pixels in the image); total red, green, and/or blue chroma; and summed luminance across subsets of pixels (e.g., across pixel rows and/or columns). In an illustrative example, the motion model outputs a binary classification (e.g., 'acceptable motion' or 'unacceptable motion') based on the first motion dataset; the body region contact model outputs a binary classification (e.g., 'finger detected' or 'finger not detected') based on a first subset of the image attributes (e.g., total luminance, total red chroma, and total blue chroma for each frame of the video segment); and the placement model outputs a binary classification (e.g., 'acceptable finger placement' or 'unacceptable finger placement') and/or a multiclass classification (e.g., 'acceptable finger placement', 'finger pressure too high', 'finger pressure too low', 'finger too far down', 'finger too far up', 'finger too far left', 'finger too far right', 'finger motion too high', etc.) based on a second subset of the image attributes (e.g., an array of summed row luminance and summed column luminance for each frame of the video segment). A final data quality classification for the video segment ('high quality' or 'low quality') can be determined based on a combination of the outputs of the motion model, body region contact model, and placement model, wherein all three models must indicate acceptable conditions (e.g., 'acceptable motion', 'finger detected', and 'acceptable finger placement') for the video segment to be classified as 'high quality'. The cardiovascular parameter module can determine a cardiovascular parameter of the user based on PG data extracted from a video classified as 'high quality' (e.g., the video segment, aggregated 'high quality' video segments, etc.).

3. Technical Advantages

Variants of the technology can confer one or more advantages over conventional technologies.

First, variants of the technology can check a quality of data to be used in determining a user or patient's cardiovascular parameters, which can help ensure that the outputs (e.g., the cardiovascular parameters) are reliable and/or accurate. Based on the data quality, the data can be used in the determination or can be recollected. For example, machine learning can be used to assess or characterize a quality of the collected data.

Second, variants of the technology can be operated or operable on a user device. For example, splitting a machine learning model into submodels (e.g., a motion model, a body region contact model, and a placement model) can simplify training of the model, help avoid overfitting or underfitting of the model, enable the models to be run on a user device, and/or otherwise enable the models to be performed or operated on a user device. Additionally, or alternatively, the technology can leverage software and/or hardware enhancements to facilitate, speed up, and/or otherwise run the models.

Third, variants of the technology can increase efficiency of data quality determination. For example, a machine learning model can be efficient enough to output a data quality classification in substantially real time (e.g., concurrently) with data acquisition and/or data quality determination, wherein the real time data quality classification can enable a user device to accumulate high quality data in real time for cardiovascular parameter determination. In variants, the efficiency of data quality determination can be increased by reducing inputs to a data quality model. For example, a body region contact model can take as input (only) total luminescence, total red chroma, and total blue chroma (e.g., no green chroma), which can result in a small (e.g., minimum) amount of data for each video frame (e.g., 3 data values for each image) used to detect finger contact (e.g., contact presence and/or pressure). A placement model can take as input (only) summed luminance across each row and column of an image, which can result in a small (e.g., minimum) amount of data used to detect which portion of the camera lens is covered/uncovered by a user's finger (e.g., detecting finger position and/or finger pressure). In variants, the placement model can correct for edge cases that would go undetected when using only the body region contact model (e.g., a user with their finger covering only the torch). In examples, the models can be combined in parallel (e.g., concurrently evaluated, which can increase overall data quality evaluation speed) and/or in series (e.g., which can decrease computational resources by mitigating unnecessary model evaluation). In variants, the computational speed can be further increased by analyzing a subsample of images from the video segment (e.g., wherein the duration between analyzed frames is shorter than a threshold determined based on user movement speed).

However, further advantages can be provided by the system and method disclosed herein.

4. System

Figure 1B:
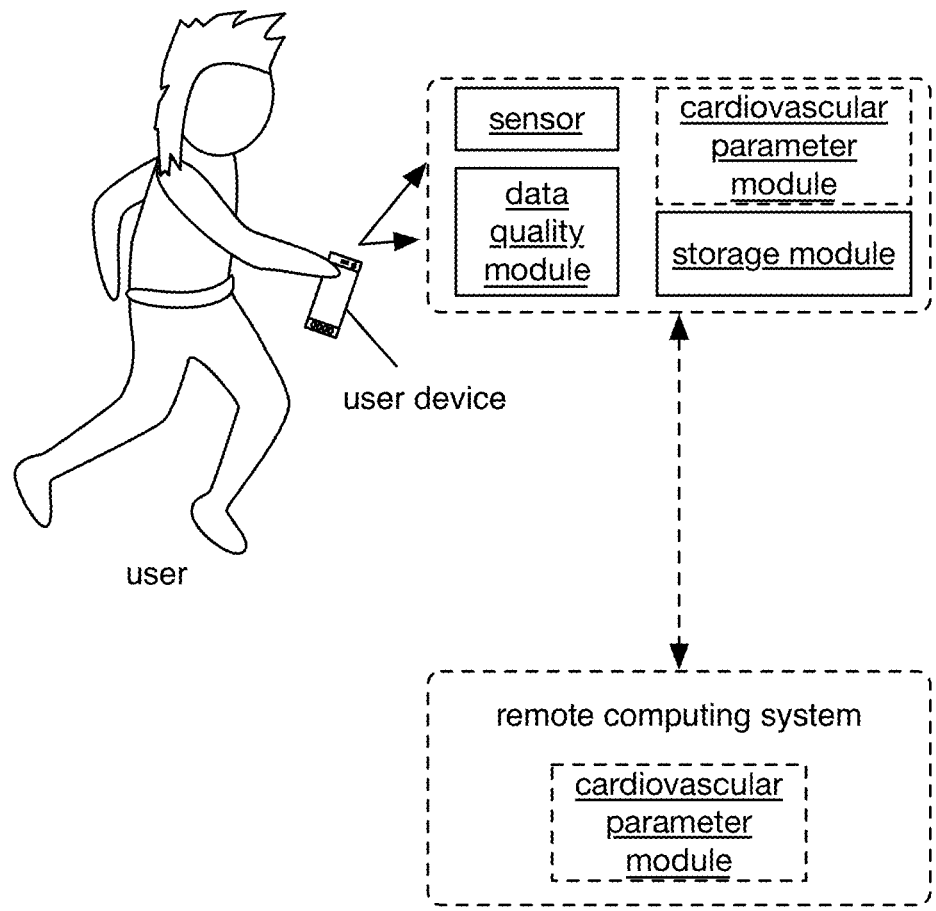
FIG. 1B is a schematic representation of an example of the system.

As shown in FIG. 1A, the system can include a sensor and a computing system. The system can be implemented on and/or distributed between: a user device, a remote computing device (e.g., cloud, server, etc.), care-provider device (e.g., dedicated instrument, care-provider smart phone, etc.), and/or at any suitable device (e.g., an example is shown in FIG. 1B). For example, a user device can include one or more sensors, the computing system, and/or any suitable components. Exemplary user devices include: smart phones, cellular phones, smart watches, laptops, tablets, computers, smart sensors, smart rings, epidermal electronics, smart glasses, head mounted displays, smart necklaces, dedicated and/or custom devices, and/or any suitable user device (e.g., wearable computer) can be used.

The system can function to acquire plethysmogram (PG) datasets, determine a quality of the PG datasets, provide feedback for how to improve the PG datasets, determine a cardiovascular parameter based on the PG datasets, and/or can otherwise function. The system is preferably implemented on (e.g., integrated into) a user device owned or associated with the user, but can be a standalone device, distributed between devices (e.g., a sensor device and a computing system device), and/or can otherwise be implemented or distributed. The system is preferably operable by a user, but can be operable by a healthcare professional (e.g., to measure a patient's data), a caregiver, a support person, and/or by any suitable person to measure a user's (e.g., patient, individual, client, etc.) cardiovascular parameter.

The sensor(s) preferably function to acquire one or more datasets where the datasets can be used to determine, process, evaluate (e.g., determine a quality of), and/or are otherwise related to a cardiovascular parameter. The sensors are preferably integrated into the user device, but can be stand-alone sensors (e.g., wearable sensors, independent sensors, etc.), integrated into a second user device, and/or can otherwise be mounted or located.

The sensors can be hardware or software sensors. For example, a gravity sensor can be implemented as a gravimeter (e.g., a hardware sensor) and/or be determined based on accelerometer (and/or gyroscope) data (e.g., a software sensor). Exemplary sensors include: accelerometers, gyroscopes, gravity sensors (gravimeters), magnetometers (e.g., compasses, hall sensor, etc.), GNSS sensors, environmental sensors (e.g., barometers, thermometers, humidity sensors, etc.), ambient light sensors, image sensors (e.g., cameras), and/or any suitable sensors. An image sensor can optionally include a torch (e.g., camera flash element, lighting element, LED, etc.).

At least one sensor is preferably configured to be arranged relative to a body region of a user (e.g., in contact with the body region, oriented relative to the body region, etc.), but alternatively can be not connected or related to the body region, and/or can be otherwise configured relative to the body region. The body region can be a finger, wrist, arm, neck, chest, ankle, foot, toe, leg, head, face, ear, nose, and/or any other body region. When more than one sensor is used, the body region can contact any sensor, all sensors, a specified sensor, and/or no sensors.

The body region can partially or fully cover a field of view (FOV) of an image sensor, but alternatively can not cover the FOV. The body region preferably covers the image sensor such that the entire FOV of the image sensor is covered by the body region, but alternatively can cover a portion (e.g., threshold portion) of the image sensor FOV or none of the FOV. The threshold extent of FOV coverage can be between 60%-100% of the FOV or any range or value therebetween (e.g., 70%, 80%, 90%, 95%, 98%, 99%, etc.), but can alternatively be less than 60%. The sensor is preferably partially or fully in physical contact with the body region, but alternatively can be a predetermined distance from the body region (e.g., a sensor for ambient light can be not in contact with the body region) or otherwise arranged. The threshold extent of contact coverage can be between 60%-100% of the image sensor (e.g., a lens on the image sensor and/or a torch of the image sensor, a portion of a lens on the image sensor corresponding to the FOV, etc.) or any range or value therebetween (e.g., 70%, 80%, 90%, 95%, 98%, 99%, etc.), but can alternatively be less than 60%. For example, the sensor can be an image sensor including a camera element and a torch, wherein the body region is in contact with both the camera element (e.g., a lens of the camera element) and the torch.

The sensor can have a predetermined pose (e.g., including position and/or orientation) or range of poses relative to the body region, but alternatively can not have a predetermined pose relative to the body region. The orientation of the body region with respect to the sensor can include an angle between a reference axis on the body region (e.g., central axis of a finger) and a reference axis on the sensor (e.g., an axis in the plane of the image sensor lens). The system is preferably agnostic to the orientation of the body region with respect to the sensor, but alternatively the orientation can be within a threshold angle and/or be otherwise arranged. The threshold orientation can be between $-180°$-$180°$ or any range or value therebetween (e.g., $-90°$-$90°$, $-45°$-$45°$, $-20°$-$20°$, $-10°$-$10°$, etc.). A reference point on the body region (e.g., a center of a fingertip) is preferably located within a threshold distance (e.g., in the plane of the image sensor lens) from a center of the sensor (e.g., a center of the image sensor lens), but can be otherwise arranged. The threshold distance can be between 0 mm-10 mm or any range or value therebetween (e.g., 5 mm, 4 mm, 3 mm, 2 mm, 1 mm, etc.), but can alternatively be greater than 10 mm. In specific examples, a threshold distance in a first direction (e.g., y-direction) can be different than a threshold distance in a second direction (e.g., x-direction).

A contact pressure (between the body region and the sensor) is preferably within a threshold pressure range as too light of a pressure can make measurements difficult and too large of a pressure can led to artifacts and inaccurate measurements. The threshold pressure range can include pressure values between 1 oz-50 oz or any range or value therebetween (e.g., 2 oz-15 oz, 3 oz-10 oz, 4 oz-10 oz, etc.), but can alternatively be less than 1 oz or greater than 50 oz. In an illustrative example, the contact pressure is approximately the weight of a smartphone. However, there can be no limits (e.g., only an upper bound, only a lower bound, no bounds) to the contact pressure. The contact pressure can be instructed (e.g., via user instructions displayed on the user device), inferred (e.g., based on FOV coverage, using the placement model, etc.), measured (e.g., using a pressure or force sensor), otherwise determined, and/or uncontrolled.

When more than one sensor is used, each sensor preferably acquires data contemporaneously or simultaneously with the other sensors, but can acquire data sequentially, interdigitated and/or in any order. Each sensor can be synchronized with or asynchronous from other sensors. The sensor rate for a sensor to acquire data can be between 10 Hz-1000 Hz or any range or value therebetween (e.g., 30 Hz-240 Hz, 60 Hz-120 Hz, etc.), but can alternatively be less than 10 Hz or greater than 1000 Hz. In general, each sensor can acquire data at a different sensor rate. In an illustrative example, a sensor used to acquire motion datasets can acquire data at a sensor rate less than a sensor rate from an image sensor (e.g., by half, 60 Hz less, 30 Hz less, etc.). However, the sensor rates can be the same, datasets can be modified (e.g., interpolated, extrapolated, culled, etc.) such that the data rates are the same, and/or the sensors can have any suitable data rates.

The datasets acquired by the sensor(s) can include PG datasets, images (e.g., image sets, intensity, chroma data, etc.), motion datasets (e.g., accelerometer data, gyroscope data, gravity vector, significant motion data, step detector data, magnetometer data, location data, etc.), image subsets (e.g., pixels, super pixels, pixel blocks, pixel rows, pixel columns, pixel sets, features, etc.), temperature datasets, pressure datasets, depth datasets (e.g., associated with images), audio datasets, and/or any suitable datasets. PG datasets are preferably photoplethymogram (PPG) datasets (sometimes referred to as photoelectric plethysmogram), but can additionally or alternatively include strain gauge plethysmograms, impedance plethysmograms, air plethysmograms, water plethysmograms, and/or any suitable plethysmograms or datasets.

Images can be 2D, 3D, and/or have any other set of dimensions. The images can be captured in: RGB, hyperspectral, multispectral, black and white, grayscale, panchromatic, IR, NIR, UV, thermal, and/or any other wavelength. The sensor can acquire images at a frame rate between 10 frames per second (FPS)-1000 FPS or any range or value therebetween (e.g., 30 FPS-1000 FPS, 50 FPS-500 FPS, greater than 60 FPS, greater than 100 FPS, greater than 120 FPS, etc.), but can alternatively acquire images at a frame rate less than 10 FPS or greater than 1000 FPS. The images can optionally be downsampled (e.g., downsampling the frame resolution for input to the data quality module and/or the cardiovascular parameter module), cropped, and/or otherwise processed.

The images can optionally be transformed. In a first example, an image is transformed based on ambient light conditions (e.g., based on ambient light measurement sampled by ambient light sensor). In a specific example, the image is transformed such that the transformed image corresponds to a target ambient light condition (e.g., wherein the target ambient light condition was used during the data quality module training via S500 methods). In a second example, an image acquired using a first sensor (e.g., a new user device make/model) is transformed such that the transformed image corresponds to a target sensor (e.g., a previous user device make/model). In a specific example, the target sensor was used during the data quality module training (e.g., via S500 methods).

One or more images (e.g., each video frame, a subset of video frames, etc.) can be decomposed into one or more channels specific to one or more of: luma and/or luminance (e.g., an amount of light that passes through, is emitted from, and/or is reflected from a particular area), chroma and/or saturation (e.g., brilliance and/or intensity of a color), hue (e.g., dominant wavelength), intensity (e.g., average of the arithmetic mean of the R, G, B channels), and/or any other parameter (e.g., a light scattering parameter including reflection, absorption, etc.).

One or more image attributes can optionally be extracted from one or more images. The image attribute is preferably a characteristic of the image itself, but can additionally or alternatively be a characteristic of the scene or subject depicted within the image. The image attributes can optionally be downsampled (e.g., to reduce data size for input to the data quality module and/or the cardiovascular parameter module). In a specific example, PG data can be an image attribute extracted from one or more images. However, PG data can be determined from other image attributes, from image features, based on light absorption characteristics, and/or otherwise determined.

An image attribute can be extracted from a set of pixels in an image. In a first embodiment, the set of pixels includes all pixels in the image. In a second embodiment, the set of pixels is a subset of the pixels in the image (e.g., an image subregion). In a first example, the subset of pixels corresponds to one or more pixel rows and/or columns (e.g., each row and/or each column, every other row and/or column, one or more rows and/or columns at an edge of the image, etc.). In a second example, the subset of pixels is a pixel block. In a third example, the subset of pixels is a super pixel. In a fourth example, the subset of pixels corresponds to a body region (e.g., a subset of pixels corresponding to a portion of a body region in a FOV of the image sensor and/or in physical contact with the image sensor). In a fifth example, the subset of pixels correspond to pixels within a predetermined image region (e.g., center region, upper right, upper left, upper middle, lower right, lower middle, lower left, right middle, left middle, etc.).

In a first variant, the image attribute can be an aggregate luminance for the set of pixels. Aggregate luminance can be a sum (e.g., total; unweighted, weighted, etc.) of luminance values, average (e.g., unweighted, weighted, etc.) luminance values, and/or any other statistical measure. In a first specific example, total luminance across an entire image (e.g., video frame) can be used to determine a data quality and/or to generate a PG dataset. In a second specific example, the aggregate luminance for one or more subsets of pixels (and/or comparison between the subsets' aggregate luminance) can indicate which portion of the image sensor FOV is covered (e.g., wherein a brighter set of pixels indicates more light leakage from ambient light and/or the torch or flash of the image sensor, which can correspond to less coverage).

In a second variant, the image attribute can be an aggregate chroma for a set of pixels. The aggregate chroma can be a sum of chroma values, average chroma values, and/or any other statistical measure. Chroma values can correspond to red chroma, blue chroma, green chroma, and/or any other hue. In a specific example, image attributes do not include green chroma. In a first example, the chroma can be aggregated across an entire image. In a second example, the chroma can be aggregated for pixel subsets (e.g., a set of rows, a set of columns, pixel blocks, etc.).

In a third variant, the image attribute can be an aggregate intensity for a set of pixels. The aggregate intensity can be a sum of intensity values, average intensity values, and/or any other statistical measure. In a first example, the intensity can be aggregated across an entire image. In a second example, the intensity can be aggregated for pixel subsets (e.g., a set of rows, a set of columns, pixel blocks, etc.).

In a fourth variant, the image attribute can be a color parameter metric for a set of pixels. For example, a model can output the color parameter metric (e.g., multiclass, binary, value, etc.) based on luminance values (and/or any other color parameter values) for all or a subset of pixels in an image. The color parameter metric can represent a pattern of color parameters (e.g., a pattern of luminance values) across the pixels in the image.

In a fifth variant, the image attribute can be a gradient, maximum value, minimum value, location of a maximum and/or minimum value, a percent of image frame, and/or any other frame-level summary for one or more color parameters (e.g., luminance, chroma, intensity, etc.).

In a sixth variant, the image attribute can be an aggregate depth for a set of pixels in an image (e.g., wherein the aggregate depth can be determined from depth values acquired from the image sensor used to acquire the image and/or a separate sensor, using optical flow, stereoscopic methods, photogrammatic methods, etc.).

Figure 13:
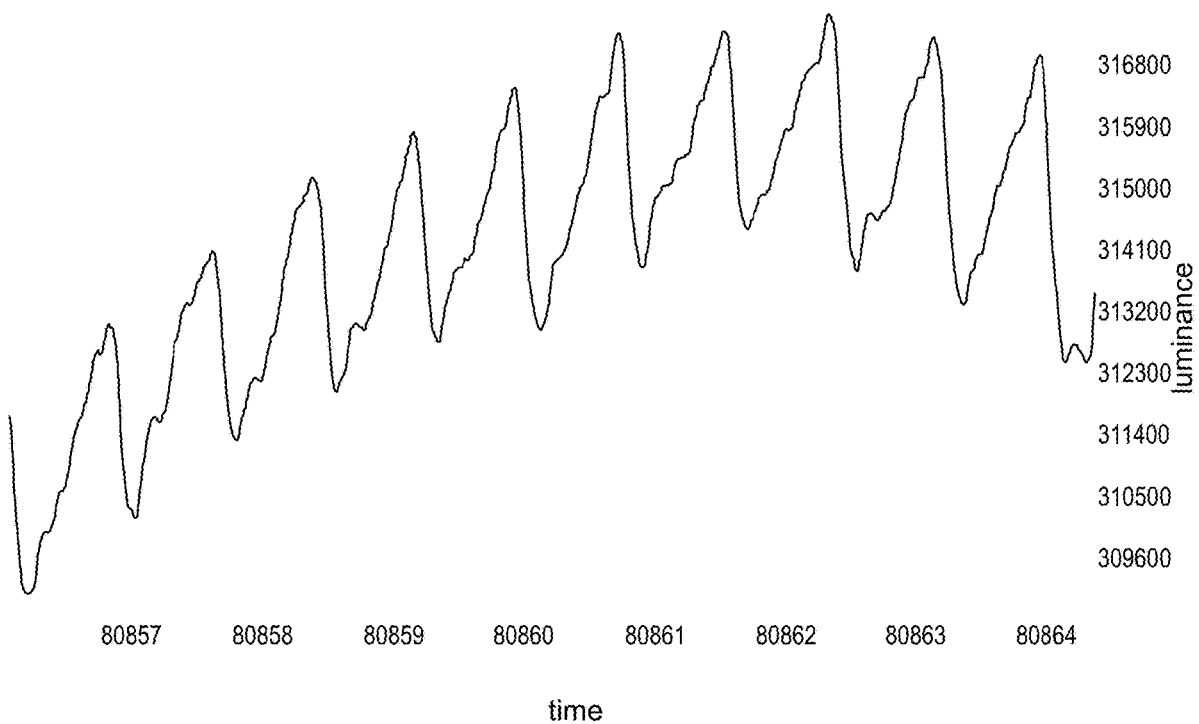
FIG. 13 depicts an example of a timeseries of total luminance.
Figure 14:
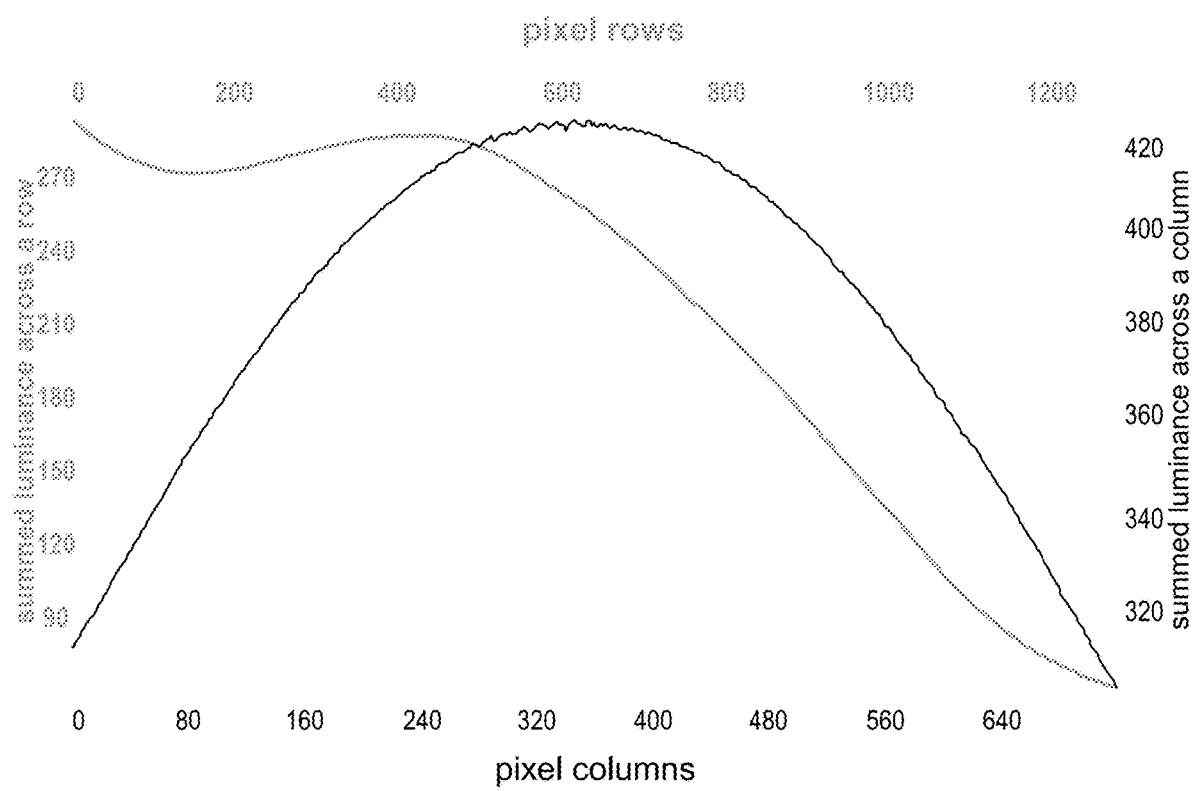
FIG. 14 depicts an example of summed luminance values rows and columns of an image.
Figure 15:
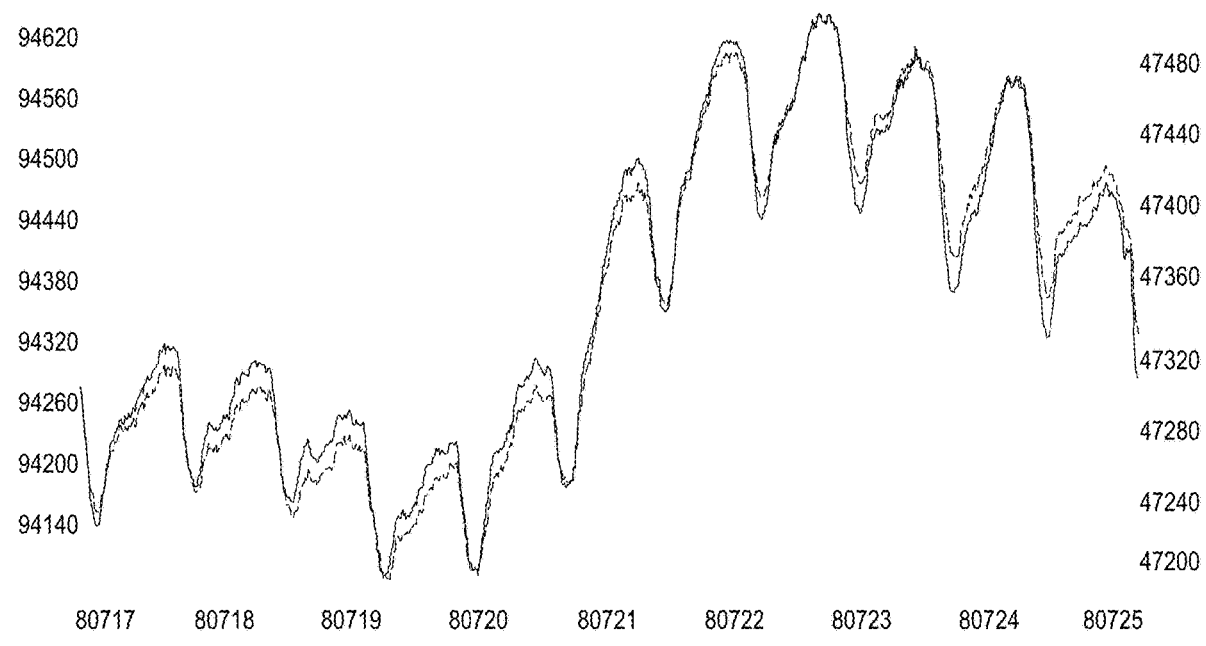
FIG. 15 depicts an example of a timeseries of total red and blue chroma.

An image attribute can optionally be aggregated across a set of images (e.g., a video). In examples, the image attribute can be individually aggregated for each of a set of images (e.g., an array including a total luminance value for each frame), individually aggregated for a subset of the set of images, aggregated across the entire set of images (e.g., a single luminance value for the entire set of images), aggregated across a subset of frames, and/or otherwise aggregated. The aggregated image attribute can be: a timeseries of image attribute values (e.g., for each successive video frame), a trend (e.g., determined from the timeseries), an statistical measure (e.g., sum, min, max, mean, median, standard deviation, etc.) across the set of images (e.g., averaged attribute value from each image; an attribute determined from an average of the images, etc.), and/or be any other suitable aggregated image attribute. In a first specific example, the aggregated image attributes can include a time series of total luminance (e.g., an array including a total luminance value for each video frame); an example is shown in FIG. 13. In a second specific example, the aggregated image attributes can include a timeseries of total red chroma and/or total blue chroma; an example is shown in FIG. 15. In a third specific example, the aggregated image attributes can include a timeseries of an array of summed luminance values (e.g., luminance summed across each pixel row and each pixel column); an example is shown in FIG. 14.

However, the sensor can be otherwise configured.

The computing system preferably functions to determine the cardiovascular parameter, evaluate a quality of the datasets, process the sensor data, and/or can otherwise function. The computing system can include one or more: general purpose processors (e.g., CPU, GPU, etc.), microprocessors, accelerated processing units (APU), machine learning processors (e.g., deep learning processor, neural processing units, tensor processing units, etc.), and/or any suitable processor(s).

The computing system can include a data quality module, a cardiovascular parameter module, a storage module, and/or any suitable module(s).

The computing system can be local (e.g., integrated into the user device, a stand-alone device, etc.), remote (e.g., a cloud computing device, a server, a remote database, etc.), and/or can be distributed (e.g., between a local and a remote computing system, between one or more local computing systems, etc.). In a first specific example, the data quality module can be implemented locally on a user device (e.g., to leverage the speed of edge computing for rapid data quality analysis and/or minimize the amount of data that needs to be sent to a remote computing system) while all or parts of the cardiovascular parameter module can be implemented on a remote system. In a second specific example, the data quality module and the cardiovascular parameter module can be implemented locally on a user device.

The data quality module preferably functions to evaluate (e.g., determine, assess, etc.) a quality of the datasets (particularly but not exclusively the PG dataset and/or data associated with the PG dataset). Evaluating the quality can include detecting outliers or inliers within a dataset, determining (e.g., estimating, predicting) whether the system (e.g., sensors thereof) was used correctly, detecting motion (or other potential sources of artifacts or inaccuracies) in the data, detecting issues with the sensors (e.g., due to bias, broken or damaged sensors, etc.), and/or otherwise evaluating whether any degradation or inadequacies are present in the data. In a specific example, the data quality module can detect if a user moved during data collection and/or a body region placement of the user on a sensor (e.g., whether the body region covered the sensor, a contact pressure applied, etc.). However, the data quality module can detect any suitable aspects associated with the data quality.

The data quality module is preferably implemented on a user device or other local system, but alternatively can be partially or fully implemented on a remote system.

The data quality module can use one or more of: machine learning (e.g., deep learning, neural network, convolutional neural network, etc.), statistical analysis, regressions, decision trees, thresholding, classification, rules, heuristics, equations (e.g., weighted equations, etc.), selection (e.g., from a library), instance-based methods (e.g., nearest neighbor), regularization methods (e.g., ridge regression), Bayesian methods (e.g., Naïve Bayes, Markov), kernel methods, probability, deterministics, genetic programs, support vectors, and/or leverage any suitable algorithms or methods to assess the data quality. The data quality module can be trained using supervised learning, unsupervised learning, reinforcement learning, semi-supervised learning, and/or in any manner (e.g., via S500 methods).

Inputs to the data quality module can include: sensor data (e.g., images, motion data, etc.), auxiliary sensor data (e.g., images, lighting, audio data, temperature data, pressure data, etc.), information derived from sensor data (e.g., image attributes), historical information (e.g., historic image attributes from data collected from the same or different user during prior measurement sessions), user inputs, user parameters (e.g., user characteristics, height, weight, gender, skin tone, etc.), environmental parameters (e.g., weather, sunny, ambient lighting, situational information, auditory information, temperature information, etc.), sensor and/or user device make/model information (e.g., camera angle, solid angle of reception, type of light sensor, etc.), body region model (e.g., a light scattering model, etc.), light source (e.g., artificial light, natural light, direct light, indirect light, etc.), ambient light intensity, and/or any suitable information. In a first example, the inputs include one or more attributes (e.g., image attributes) extracted from sensor data. In a second example, the inputs include one or more features extracted from sensor data (e.g., features depicted in image, peaks, derivatives, etc.).

Inputs (particularly but not exclusively data) are preferably associated with a time window, but can include all historical data, predetermined historical data, current data, and/or any suitable data. The time window can depend on a target amount of data for determining the cardiovascular parameters (e.g., a threshold length of time), a processor capability, a memory limit, a sensor data rate, a number of data quality modules, and/or on any suitable information. The time window can be between 0.5 s-600 s or any range or value therebetween (e.g., 0.5, 1 s, 2 s, 4 s, 5 s, 8 s, 10 s, 12 s, 15 s, 20 s, 25 s, 50 s, 100 s, etc.), but can alternatively be less than 0.5 s or greater than 600 s. The time window can be a running time window (e.g., a time window can overlap another time window), sliding time window, discrete time windows (e.g., nonoverlapping time windows, nonconsecutive time windows, consecutive time windows, etc.), and/or any suitable time window. The dataset can be contiguous or noncontiguous. The dataset can optionally be a data segment (e.g., corresponding to a time window within a larger time range), wherein multiple data segments can optionally be aggregated (e.g., via S300 methods).

Outputs from the data quality module can include: a data quality, processed data (e.g., data processed to ensure that it achieves a target quality or metric), a flag (e.g., indicative of 'good' or 'bad' data), instructions to use (or possibly how to use or process) the data, instructions for how to improve the data collection, sensor use information (e.g., contact pressure, degree of coverage, orientation, etc.), a state of the user and/or system (e.g., a motion state, a use state, etc.), and/or any suitable outputs. The data quality can be a score, a classification, a probability (e.g., a probability of a given data quality, a probability of data being used to achieve a target or minimum accuracy or precision cardiovascular parameter, etc.), a quality, instructions, a flag, and/or any suitable output. The data quality can be binary (e.g., good vs bad, sufficient vs insufficient, yes vs no, useable vs unusable, acceptable vs unacceptable, etc.), a score, continuous (e.g., taking on any value such as between 0 to 1, 0 to 0, 0 to 100, $-\infty$ and $\infty$, etc.), discrete (e.g., taking on one of a discrete number of possible values, multiclass, etc.), and/or any suitable quality. The data quality can be a quality corresponding to input data and/or any other data. For example, when the input data includes image attributes extracted from sensor data (e.g., a video), the data quality can be a data quality for the input image attributes, for the sensor data, for PG data and/or any other image attributes extracted from the sensor data, and/or any other data. In some instances, the outputs from one or more data quality modules can be combined and/or processed to provide instructions, recommendations, guidance, and/or other information to the user (for example to improve or enhance a data quality for data to be collected).

The data quality can optionally be compared to one or more criteria (e.g., evaluating whether the data quality indicates high or low quality data, acceptable or unacceptable conditions, etc.). A criterion can be a threshold, a value (e.g., the data quality must equal a value), a presence/absence of a flag, and/or any other criterion. When the data quality meets one or more criteria: data can be stored, PG data can be generated (e.g., using images associated with the data quality), a cardiovascular parameter can be determined from PG data associated with the data quality, and/or any other action can be performed. When the data quality does not meet one or more criteria: the user can be guided (e.g., based on the data quality), data associated with the data quality can be rejected (e.g., erased, not stored, etc.), all or parts of the method can be reset and/or restart (e.g., acquiring new data), and/or any other action can be performed.

Figure 3:
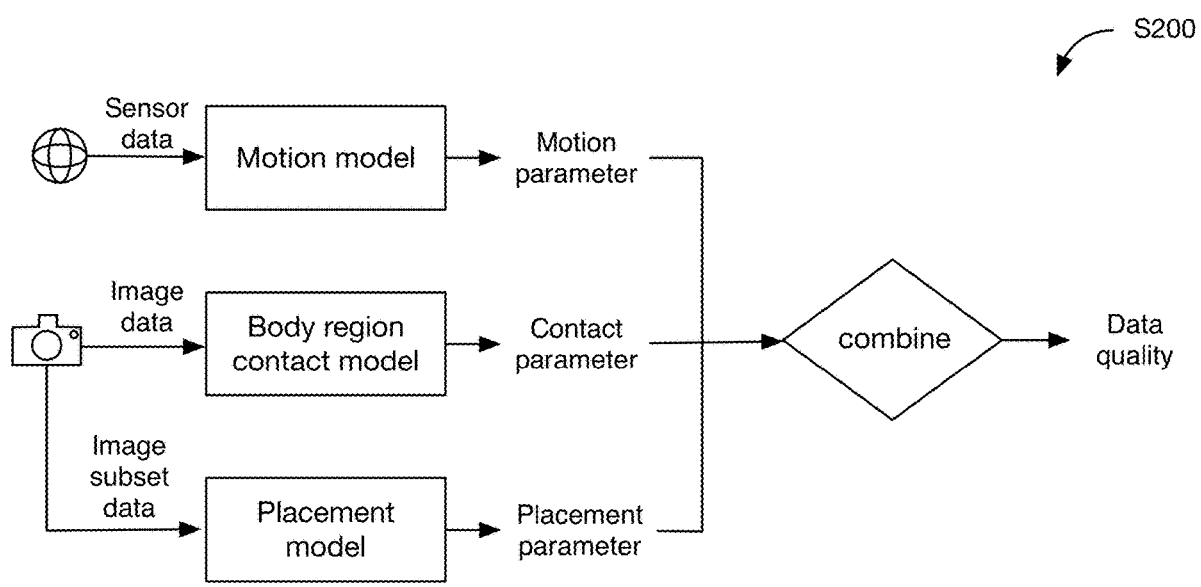
FIG. 3 depicts an example of combining outputs of a motion model, a body region contact model, and a placement model.

The system can include one or more data quality modules. When the system includes a plurality of data quality modules, the data quality modules can be correlated and/or uncorrelated from one another. Typically, each of the data quality modules uses different inputs, but one or more data quality modules can use the same inputs. Each of the data quality modules can provide the same or different outputs. Data quality modules, models included in a data quality module, and/or outputs thereof (e.g., the data quality, the classification of the PG dataset, etc.) can be combined (e.g., averaged, weighted average, using logical operators, using a set of rules, using voting, etc.), compared, selected from, voted on (e.g., using voting to select a most likely data quality; ranked voting, impartial voting, consensus voting, etc.), can be used separately, and/or can otherwise be used in tandem or isolation. In examples, logical operators used to combine one or more data quality modules and/or outputs therefrom can include: 'AND', 'OR', 'XOR', 'NAND', 'NOR', 'XNOR', 'IF/THEN', 'IF/ELSE', and/or any other operator. An example is shown in FIG. 3. For example, when one model classifies the PG dataset as having a low quality (e.g., 'bad', score less than a threshold, 'poor', 'insufficient', etc.), then the combined classification of the PG dataset can be low quality (e.g., even if the remaining the data quality modules indicate that the data quality is "good"). In a specific example, the logical operator between multiple data quality module outputs is an AND operator, wherein all data quality modules must output a 'good' score (e.g., indicating high quality data) in order for the data quality associated with input images (e.g., associated with PG data extracted from the input images) to be classified 'good'. However, the data quality modules and/or outputs thereof can otherwise be combined.

Data quality modules can include a motion model, a body region contact model, a placement model, and/or any other model. Models can be specific to: a user device make and/or model, a sensor (e.g., camera or other image senor, motion sensor, etc.) make and/or model, a specific sensor instance, an environmental parameter, a user parameter, and/or any other parameter.

The motion model can function to determine a motion parameter for the user and/or user device. The motion parameter preferably indicates whether the user and/or the user device is moving (e.g., motion exceeds a threshold speed, motion exceeds a threshold acceleration, motion exceeds a threshold distance, etc.) and/or was moving within a threshold time period. Additionally or alternatively, the motion parameter can indicate whether the user pose and/or user device pose is within a threshold pose range. However, the motion parameter can indicate any metric (e.g., any data quality metric). One or more thresholds defining acceptable and/or unacceptable motion (e.g., wherein acceptable motion corresponds to high quality data and/or wherein unacceptable motion corresponds to low quality data) can optionally be defined (e.g., empirically defined) during model training (e.g., S500), but can additionally or alternatively be predetermined, be otherwise determined, and/or not be used for the motion model.

The motion model can include a classifier, set of thresholds for each input, heuristic, machine learning model (e.g., NN, CNN, DNN, etc.), statistical analysis, regressions, decision trees, rules, equations, selection, instance-based methods, regularization methods, Bayesian methods, kernel methods, probability, deterministics, genetic programs, support vectors, and/or any other model. The motion model is preferably a single model outputting a motion parameter (e.g., a binary classification), but can alternatively be multiple models wherein the motion parameter output is determined from multiple model outputs.

The motion model can receive as inputs: accelerometer data (e.g., in one or more of x/y/z coordinates), gyroscope data (e.g., in one or more of x/y/z coordinates), gravity vector data (e.g., in one or more of x/y/z coordinates), location information, environmental data, and/or any other suitable data (e.g., any other data quality module input data). In an example, the motion model input includes gravity (e.g., xyz vector), acceleration (e.g., xyz vector), rotation (e.g., xyz vector), and attitude (e.g., vector including pitch, yaw, and roll). In a specific example, the motion model input includes only gravity, acceleration, rotation, and attitude. The input data is preferably concurrently sampled with the measurements used for other data quality modules and/or cardiovascular parameter modules, but can alternatively be contemporaneously sampled, asynchronously sampled, and/or otherwise sampled relative to other modules.

The motion model can output the motion parameter, wherein the motion parameter can be a classification (e.g., binary, multiclass, etc.), a score, continuous, discrete, and/or be any other parameter type. In examples, the motion parameter can be associated with: user and/or user device motion, user and/or user device pose (e.g., position and/or orientation), a data quality (e.g., a data quality classification for the input data and/or for a PG dataset associated with the input data), a combination thereof, and/or any other parameter.

In specific examples, the motion model can output a classification of a user or user device motion (e.g., a yes/no classification for whether the user is moving, a yes/no classification for whether the user has moved recently, a good/bad classification for whether the user device is experience acceptable/unacceptable motion, etc.), a value for the user or user device motion, a classification of user and/or user device pose, a classification of a PG dataset (e.g., a PG dataset that was acquired concurrently or contemporaneously with the input data, a PG dataset derived from the input data, etc.), guidance for adjusting (e.g., improving) user and/or user device motion, and/or any suitable output. In a first illustrative example, the motion model can output a binary classification corresponding to 'acceptable motion' (e.g., 'correct motion') and 'unacceptable motion' (e.g., 'incorrect motion'). In a second illustrative example, the motion model can output a multiclass classification corresponding to specific acceptable and/or unacceptable conditions (e.g., the acceptable and/or unacceptable conditions in S500).

Figure 4:
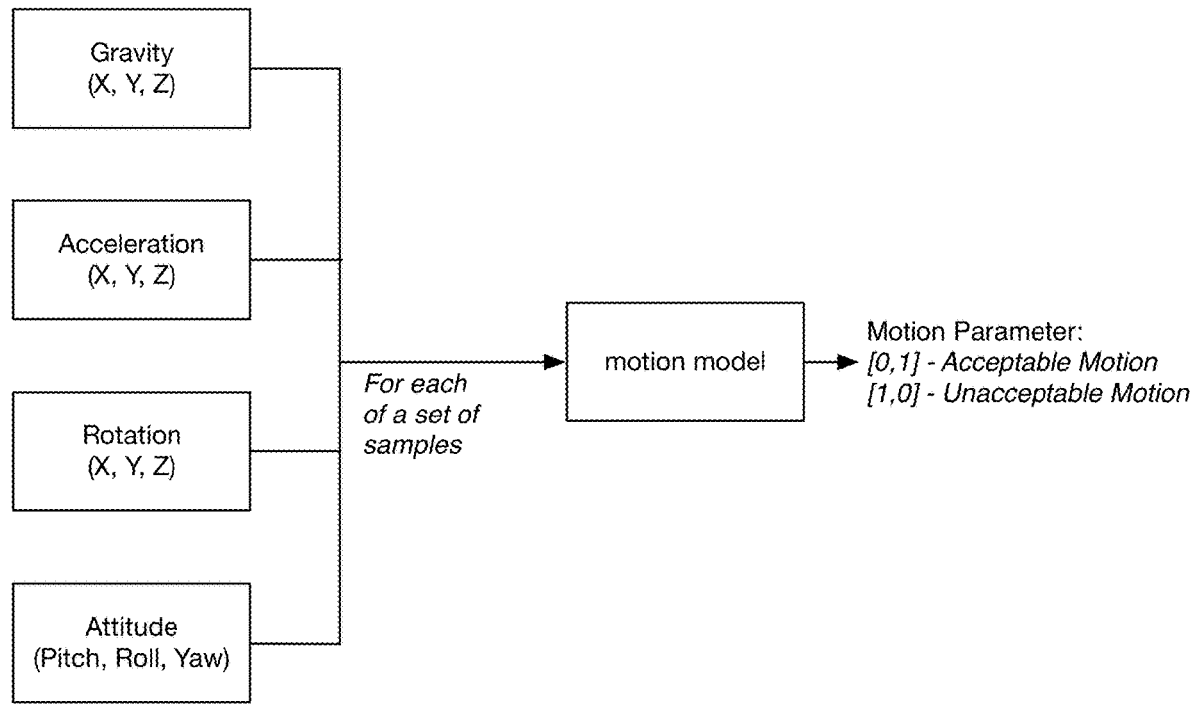
FIG. 4 depicts an example of a motion model.

An example is shown in FIG. 4.

However, the motion model can be otherwise configured.

The body region contact model (e.g., a body region detection model) can function to determine a contact parameter for a body region (e.g., a finger) relative to a sensor (e.g., image sensor). The contact parameter preferably indicates whether a body region is in contact with the sensor. Additionally or alternatively, the contact parameter can indicate whether the body region is within a FOV of a sensor (e.g., within a threshold extent of FOV coverage), whether the body region is in contact with the sensor within a threshold extent of contact coverage, whether the body region is in contact with the sensor within a threshold pressure range, and/or whether the body region pose is within a threshold pose range relative to the sensor. However, the contact parameter can indicate any metric (e.g., any data quality metric). One or more thresholds defining acceptable and/or unacceptable body region contact (e.g., wherein acceptable body region contact corresponds to high quality data and/or wherein unacceptable body region contact corresponds to low quality data) can optionally be defined (e.g., empirically defined) during model training (e.g., S500), but can additionally or alternatively be predetermined, be otherwise determined, and/or not be used for the body region contact model.

The body region contact model can include a classifier, set of thresholds for each input, heuristic, machine learning model (e.g., NN, CNN, DNN, etc.), statistical analysis, regressions, decision trees, rules, equations, selection, instance-based methods, regularization methods, Bayesian methods, kernel methods, probability, deterministics, genetic programs, support vectors, and/or any other model.

The body region contact model is preferably a single model outputting a contact parameter (e.g., a binary classification), but can alternatively be multiple models wherein the contact parameter output is determined from multiple model outputs. In a first specific example, one model functions to detect body region contact presence and/or an extent of contact coverage. In a second specific example, one model functions to detect body region contact presence, an extent of contact coverage, a body region pose, and/or a contact pressure. In a third specific example, the body region contact model includes two models, wherein a first model functions to detect body region contact presence and/or an extent of contact coverage, and a second model functions to detect contact pressure and/or body region pose.

The body region contact model can receive as inputs: image attributes, images, depth datasets, other sensor data, and/or any other suitable data (e.g., any other data quality module input data). For example, the body region contact model input can include total luminance, total chroma (e.g., total red, total blue, and/or total green chroma values; only total red and total blue chroma values; etc.), and/or any other image attribute for one or more images. The image attributes can be optionally aggregated across a set of images (e.g., an array of one or more image attribute values for each image; a single value for each image attribute corresponding to the entire set of images; etc.). In an illustrative example, the body region contact model input includes total luminance, total red chroma, and total blue chroma values for each frame of a video. In a specific example, an image sensor can sample a 2 s video at 60 FPS (120 frames), wherein a total luminance, total red chroma, and total blue chroma is determined for each frame (e.g., the input data includes three arrays with dimensions [120×1]). The input data is preferably concurrently sampled with the measurements used for other data quality modules and/or cardiovascular parameter modules, but can alternatively be contemporaneously sampled, asynchronously sampled, and/or otherwise sampled relative to other modules.

The body region contact model can output the contact parameter, wherein the contact parameter can be a classification (e.g., binary, multiclass, etc.), a score, continuous, discrete, and/or be any other parameter type. In examples, the contact parameter can be associated with: body region contact with the sensor (e.g., contact pressure, contact presence, extent of contact coverage, etc.), body region detection in a sensor FOV (e.g., body region presence, extent of FOV coverage), body region pose relative to the sensor for the body region (e.g., position and/or orientation; only the body region position; etc.), a data quality (e.g., a data quality classification for the input data and/or for a PG dataset associated with the input data), a combination thereof, and/or any other parameter.

In specific examples, the body region contact model can output a classification of a user body region coverage of the sensor (e.g., a presence/absence of the body region within a FOV of an image sensor; presence/absence of body region contact with the sensor; a yes/no classification for whether the body region contact coverage and/or FOV coverage is above a threshold value, etc.), a value for the extent of contact coverage, a classification of a contact pressure (e.g., good/bad or acceptable/unacceptable contact pressure), a value for the contact pressure, a classification of a PG dataset (e.g., a PG dataset that was acquired concurrently or contemporaneously with the input data, a PG dataset derived from the input data, etc.), guidance for adjusting (e.g., improving) body region contact, and/or any suitable output can be generated. In a first illustrative example, the body region contact model can output a binary classification corresponding to 'body region detected' and 'body region not detected'. In a second illustrative example, the body region contact model can output a multiclass classification corresponding to specific acceptable and/or unacceptable conditions (e.g., the acceptable and/or unacceptable conditions in S500).

Figure 5:
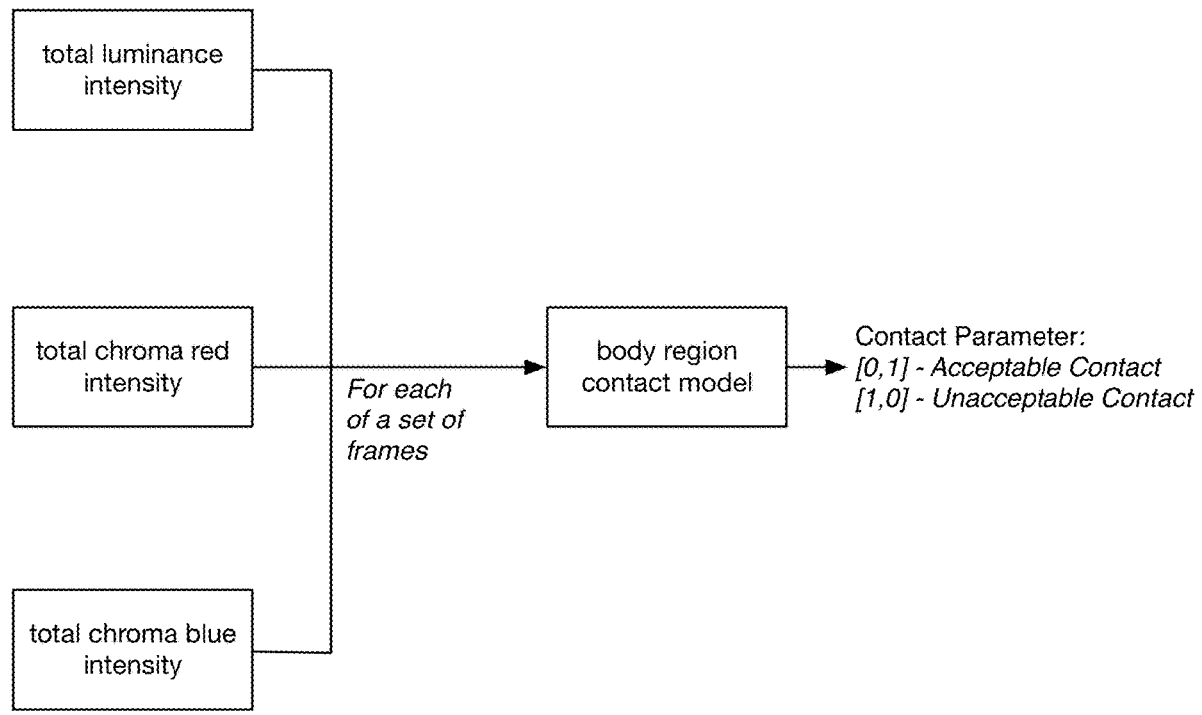
FIG. 5 depicts an example of a body region contact model.

An example is shown in FIG. 5.

However, the body region contact model can be otherwise configured.

The placement model can function to determine a placement parameter (e.g., a pose parameter, a pressure parameter, a contact parameter, etc.) for a body region (e.g., finger) relative to a sensor (e.g., image sensor). The placement parameter preferably indicates which portion of the image sensor FOV is covered by the body region. Additionally or alternatively, the placement parameter can indicate whether the body region is in contact with the sensor within a threshold pressure range, whether the body region placement is within a threshold pose range relative to the sensor (e.g., a threshold distance and/or a threshold orientation relative to the image sensor), whether a body region is within a FOV of a sensor (e.g., within a threshold extent of FOV coverage), and/or whether a body region is in contact with the sensor (e.g., within a threshold extent of contact coverage). However, the placement parameter can indicate any metric (e.g., any data quality metric). One or more thresholds defining acceptable and/or unacceptable body region placement (e.g., wherein acceptable placement corresponds to high quality data and/or wherein unacceptable placement corresponds to low quality data) can optionally be defined (e.g., empirically defined) during model training (e.g., S500), but can additionally or alternatively be predetermined, be otherwise determined, and/or not be used for the placement model.

The placement model can include a classifier, set of thresholds for each input, heuristic, machine learning model (e.g., NN, CNN, DNN, etc.), statistical analysis, regressions, decision trees, rules, equations, selection, instance-based methods, regularization methods, Bayesian methods, kernel methods, probability, deterministics, genetic programs, support vectors, and/or any other model. The placement model is preferably a single model outputting a placement parameter (e.g., a binary classification), but can alternatively be multiple models wherein the placement parameter output is determined from multiple model outputs.

Figure 7:
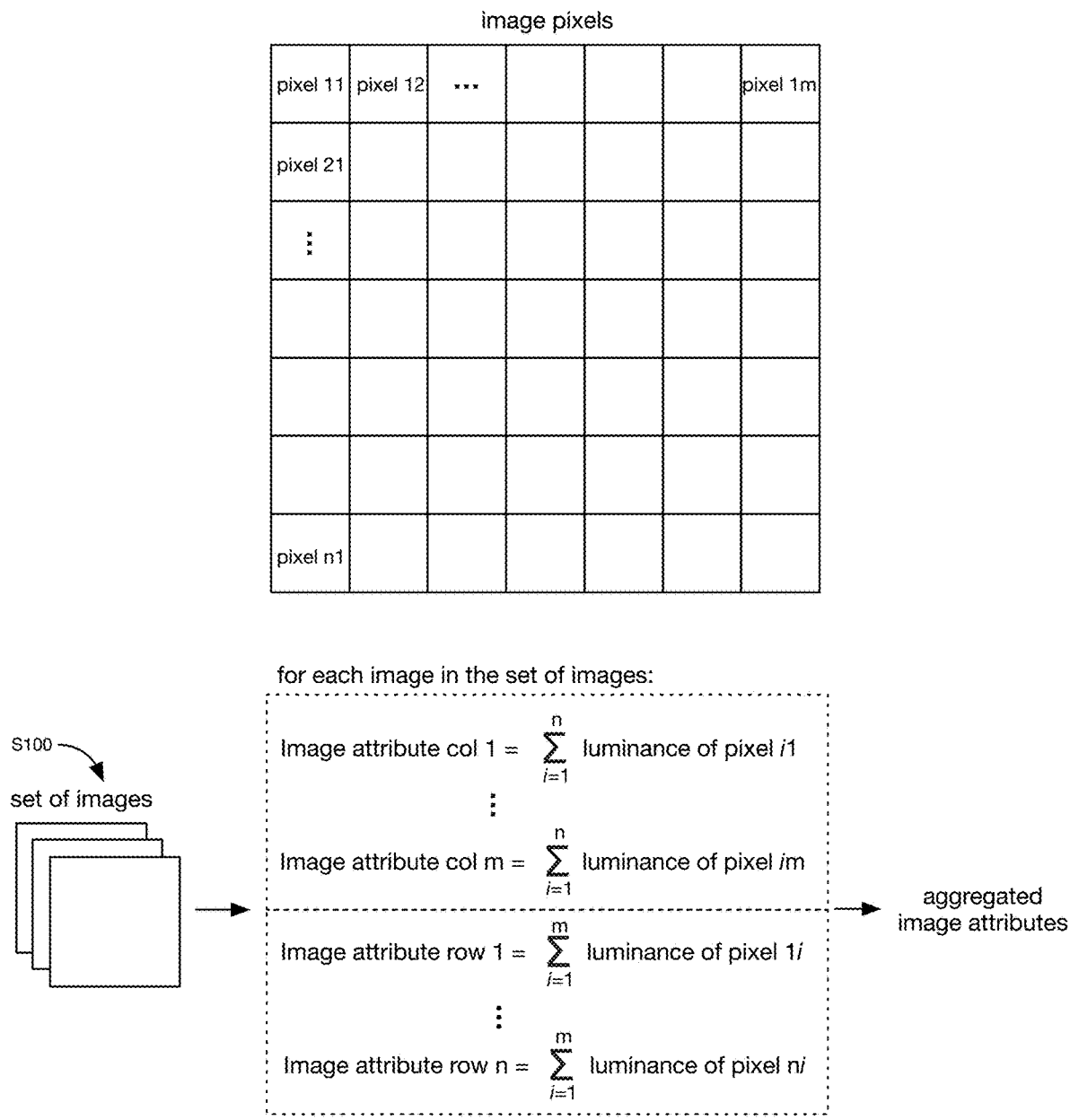
FIG. 7 depicts an example of aggregating image attributes.

The placement model can receive the same or different inputs as the body region contact model. In examples, the placement model can receive as inputs: image attributes, images, depth datasets, other sensor data, and/or any other suitable data (e.g., any other data quality module input data). For example, the placement model input can include summed luminance across a subset of pixels in an image, summed chroma (e.g., summed red, summed blue, and/or summed green chroma values) across a subset of pixels in an image, and/or any other image attribute for one or more images. The subset of pixels can be distinct image subregions and/or overlapping subregions. In an illustrative example, the placement model input includes an array of summed luminance for each pixel row and/or column of an image (e.g., each row and/or column of the entire image or a portion of the image). The image attributes can be optionally aggregated across a set of images (e.g., an array of one or more image attribute values for each image; a single value for each image attribute corresponding to the entire set of images; etc.). An example is shown in FIG. 7. In a specific example, an image sensor can sample a 2 s video at 120 FPS (120 frames), wherein each frame has a resolution of 1280× 720 pixels; a summed luminance is determined for each row (e.g., the input data across the frames includes an array with dimensions [120×1280]) and column (e.g., the input data across the frames includes an array with dimensions [120× 720]). The input data is preferably concurrently sampled with the measurements used for other data quality modules and/or cardiovascular parameter modules, but can alternatively be contemporaneously sampled, asynchronously sampled, and/or otherwise sampled relative to other modules.

The placement model can return the same or different outputs as the body region contact model. The placement model can output the placement parameter, wherein the placement parameter can be a classification (e.g., binary, multiclass, etc.), a score, continuous, discrete, and/or be any other parameter type. In examples, the placement parameter can be associated with: body region pose relative to the sensor for the body region (e.g., position and/or orientation; only the body region position; etc.), body region contact with the sensor (e.g., contact pressure, contact presence, extent of contact coverage, etc.), a data quality (e.g., a data quality classification for the input data and/or for a PG dataset associated with the input data), a combination thereof, and/or any other parameter.

In specific examples, the placement model can output a pose of the body region relative to the sensor (e.g., position and/or orientation), a classification of a pose of the body region relative to the sensor (e.g., a yes/no classification for whether the body region pose is placed within a threshold pose range, acceptable/unacceptable pose, a multiclass classification indicating the pose, etc.), a position of the body region relative to the sensor (e.g., a distance from the sensor center), a classification of a position of the body region relative to the sensor (e.g., a yes/no classification for whether the body region is placed within a threshold distance to the sensor center, acceptable/unacceptable position, a multiclass classification indicating the pose, etc.), a classification of a contact pressure (e.g., good/bad or acceptable/ unacceptable contact pressure), a value for the contact pressure, classification of a body region coverage of the sensor (e.g., a yes/no classification for whether the body region contact coverage and/or FOV coverage is above a threshold value, etc.), a value for the extent of contact coverage, guidance for adjusting (e.g., improving) placement (e.g., including pose and/or contact pressure) of the body region, instructions for how to adjust (e.g., improve) a PG dataset quality (e.g., via body region pose guidance), a classification of a PG dataset (e.g., a PG dataset that was acquired concurrently or contemporaneously with the input data, a PG dataset derived from the input data, etc.), and/or any suitable output can be generated.

In a first illustrative example, the placement model can output a binary classification corresponding to 'acceptable body region placement' and 'unacceptable body region placement'. In a second illustrative example, the placement model can output a multiclass classification corresponding to specific acceptable and/or unacceptable conditions (e.g., the acceptable and/or unacceptable conditions in S500). For example, the multiclass classification can include: 'acceptable body region placement', 'contact pressure too high', 'contact pressure too low', 'body region too far down', 'body region too far up', 'body region too far left', 'body region too far right', 'body region motion too high', and/or any other classification.

Figure 6A:
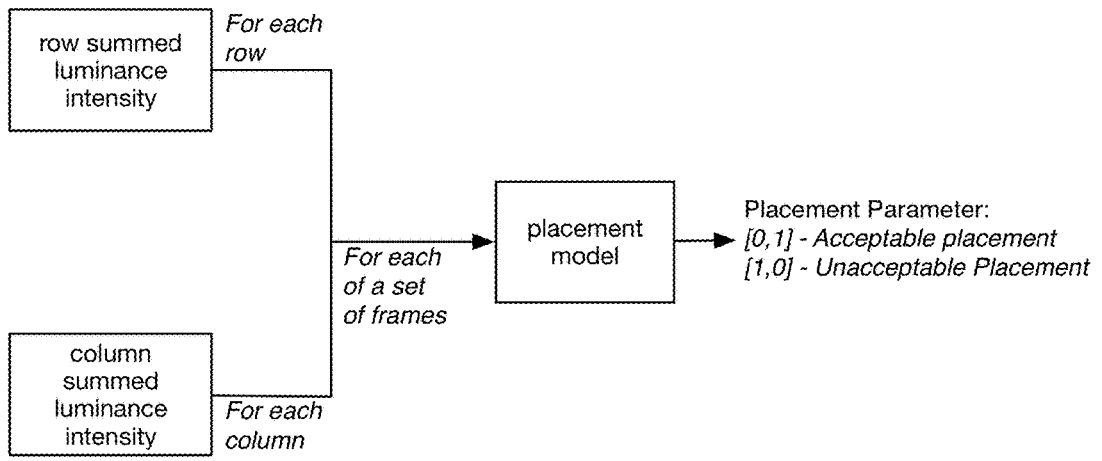
FIGS. 6A, 6B, and 6C depict examples of a placement model.
Figure 6B:
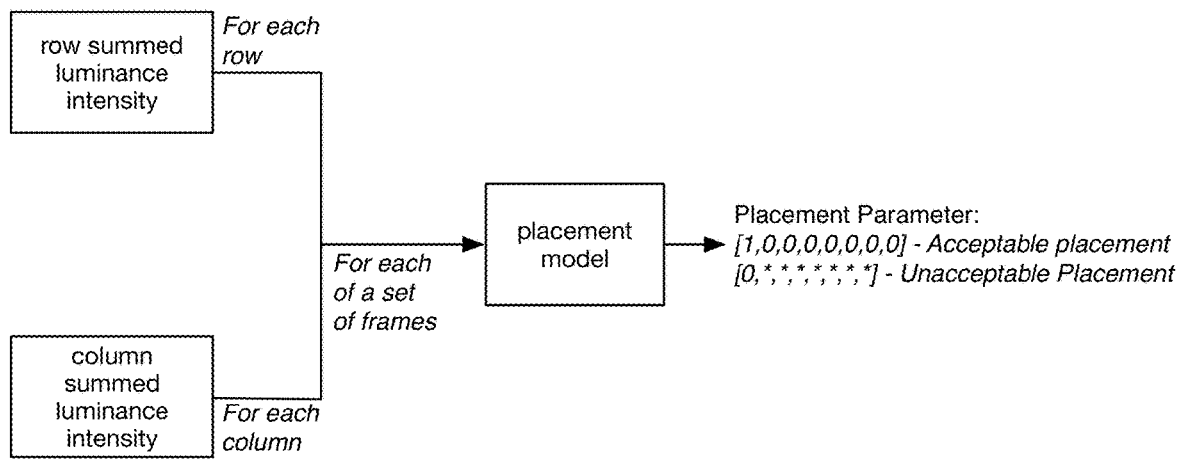
Figure 6C:
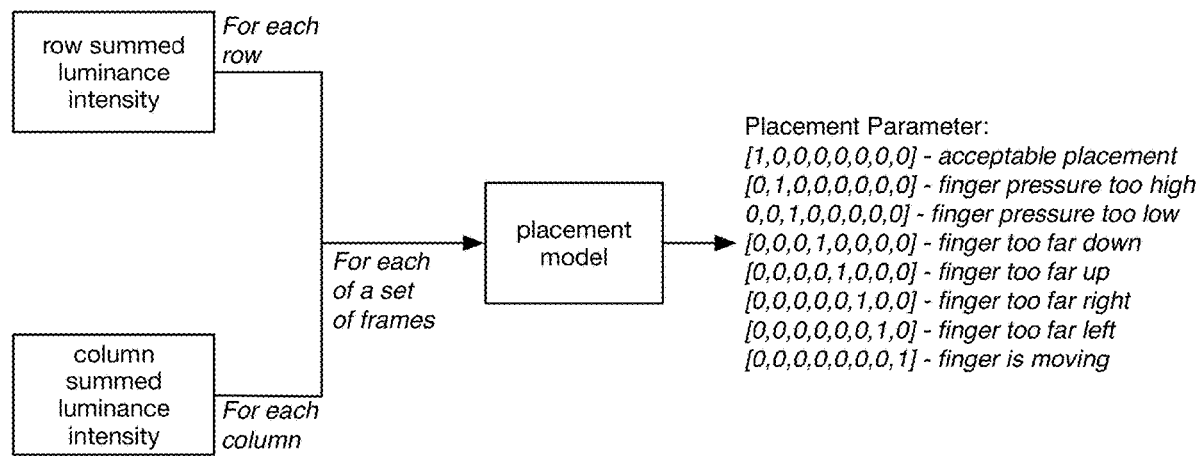

Examples are shown in FIG. 6A, FIG. 6B, and FIG. 6C.

However, the placement model can be otherwise configured.

In specific examples, two models can be used (e.g., a body region contact model and a placement model, a motion model and a placement model, a motion model and a body region contact model, etc.), three models can be used (e.g., a body region contact model, a placement model, and a motion model; a motion model and two body region contact models, etc.), more than three models can be used (e.g., duplicate models, additional models such as models that process chroma or color channels separately, etc.), and/or any suitable models can be used. Additionally or alternatively, a single model can be trained that processes the inputs and/or generates the outputs of two or more of the separated models. However, any suitable models can be used.

However, the data quality module can be otherwise configured.

A cardiovascular parameter module preferably functions to determine the cardiovascular parameter. The cardiovascular parameter module can additionally or alternatively function to determine or process (e.g., segment, denoise, etc.) a PG dataset (e.g., from a set of images, as disclosed in U.S. patent application Ser. No. 17/866,185 titled 'METHOD AND SYSTEM FOR CARDIOVASCULAR DISEASE ASSESSMENT AND MANAGEMENT' filed on 15 Jul. 2022 which is incorporated in its entirety by this reference, etc.), and/or can otherwise function.

The cardiovascular parameter module can be local, remote, distributed, or otherwise arranged relative to any other system or module. In a first example, one or more inputs are determined locally (e.g., via a user device) and transmitted to a cardiovascular parameter module implemented on a remote computing system. In this example, one or more outputs from the cardiovascular parameter module can optionally be transmitted back to a local system (e.g., the user device). In a second example, the cardiovascular module is implemented locally on a user device or other local system.

The output of the cardiovascular parameter module can be one or more cardiovascular parameters, a processed dataset (e.g., processed PG dataset), and/or any other suitable output. The cardiovascular parameter module can receive as inputs: image attributes for one or more images (e.g., PG data), image features, images, environmental parameters, other sensor data, and/or any other suitable data (e.g., any other data quality module input data). Image features are preferably different from image attributes, but can alternatively be the same as image attributes. All or parts of the input data is preferably the same data and/or extracted from the same data used by one or more data quality modules, but can alternatively not be the same data used by one or more data quality modules. For example, the cardiovascular parameter module input(s) can be derived from all or a subset of a series of images, wherein the same series of images was used to determine inputs for one or more data quality modules. In a specific example, a first set of image features and/or attributes can be extracted from a series of images to be used as input into one or more data quality modules; a second set of image features and/or attributes (e.g., PG data) can be extracted from all or a subset of the series of images (e.g., wherein the subset is determined based on the data quality module output) can be used as input in the cardiovascular parameter module.

The cardiovascular parameter(s) are preferably determined from data (e.g., PG data) that is associated with a high data quality (e.g., as determined by the data quality module(s)), but can be determined using data with a low data quality, and/or any suitable data. In a first variant, an entire sensor data sample is validated by the data quality module (e.g., validated as high data quality), wherein the validated sensor data sample and/or data extracted therefrom (e.g., image attributes and/or image features) can be used as an input into the cardiovascular parameter model. In a second variant, a portion of a sensor data is validated by the data quality module (e.g., a subset of frames in a video, a subset of pixels in one or more frames, etc.). For example, the output of the data quality modules is used to select high quality images, wherein image features and/or image attributes extracted from the high data quality images are used as inputs into the cardiovascular parameter module. In a third variant, the cardiovascular parameter input can be different from the data validated by the data quality module.

The cardiovascular parameters are preferably determined using a time series of PG data (e.g., a times series of multiple high quality PG datasets), but can be determined using any suitable data. For example, a cardiovascular parameter can be determined using PG datasets (or other datasets) that include at least a threshold number of seconds of data. The threshold number of seconds can be between 4 s-600 s or any range or value therebetween (e.g., 5 s, 10 s, 15 s, 20 s, 30 s, 45 s, 60 s, 120 s, 300 s, 600 s, etc.), but can alternatively be less than 4 s or greater than 600 s. The time series of data can be contiguous (e.g., PG data extracted from an uninterrupted segment of a video) or noncontiguous (e.g., PG data extracted from discrete, non-neighboring segments of a video). The time series of data can optionally be accumulated segments of an initial timeseries of data (e.g., accumulated via S300 methods). The segments can correspond to a predetermined length of time, a predetermined data size, a variable length of time, a variable data size, and/or any other parameter. In a first example, segment length is predetermined. The segment length can be between 0.2 s-60 s or any range or value therebetween (e.g., 0.5 s-5 s, 1 s-3 s, is, 2 s, 3 s, etc.), but can alternatively be less than 0.2 s or greater than 60 s. In a second example, segment length is determined based on one or more data quality module outputs (e.g., the segment corresponds to a segment of high data quality; a segment ends when data quality crosses a threshold from 'good' to 'bad'; etc.).

The cardiovascular parameter can be determined using a transformation, using an equation, using a machine learning algorithm, using a particle filter, any method in S400, and/or in any suitable manner.

However, the cardiovascular parameter module can be otherwise configured.

The storage module preferably functions to store the datasets and/or cardiovascular parameters. The storage module can store the datasets and/or cardiovascular parameters can locally and/or remotely. The storage modules can correspond to long-term (e.g., permanent) memory or short-term (e.g., transient) memory. Examples of storage modules include caches, buffers (e.g., image buffers), databases, look-up tables, RAM, ROM, and/or any type of memory. However, the storage module can be otherwise configured.

However, the computing system can be otherwise configured.

5. Method

As shown in FIG. 2, the method can include acquiring data S100 and determining a quality of the data S200. The method can optionally include guiding a user based on the quality of the data S250, processing the data S300, determining a cardiovascular parameter S400, training a data quality module S500, and/or any suitable steps. All or portions of the method can be performed by one or more components of the system, by a user, and/or by any other suitable system.

Figure 11:
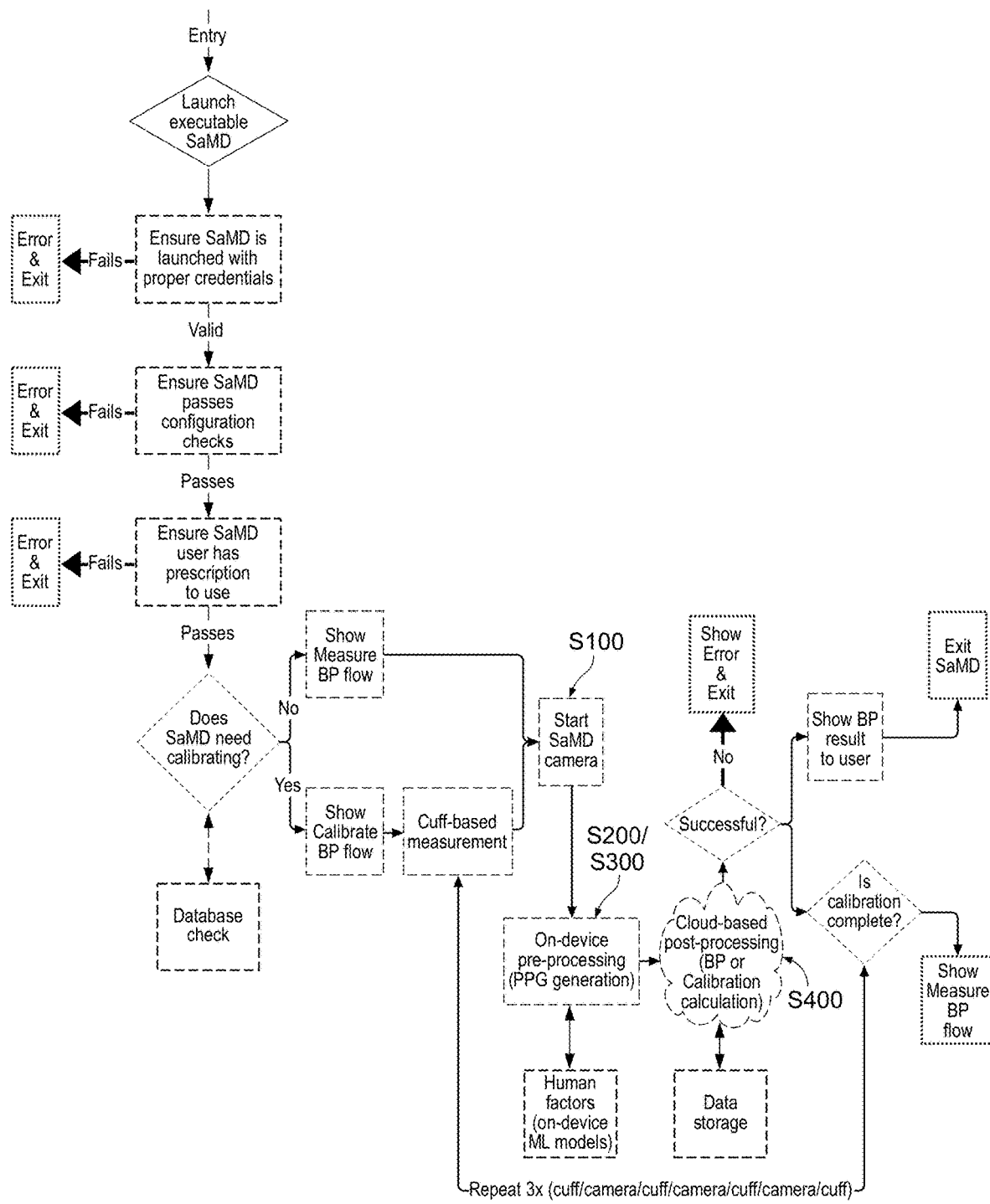
FIG. 11 depicts an example of the method.

All or portions of the method can be performed automatically (e.g., in response to one or more criteria being met), manually, semi-automatically, and/or otherwise performed. All or portions of the method can be performed after calibration (e.g., with a blood pressure cuff, ECG system, and/or any other calibration system), during calibration, without calibration, and/or at any other time. An example of the method including calibration is shown in FIG. 11. All or portions of the method can be performed in real-time (e.g., data can be processed contemporaneously with and or concurrently with data acquisition), offline (e.g., with a delay or lag between data acquisition and data processing), iteratively, asynchronously, periodically, and/or with any suitable timing. In an example, the method can include acquiring data segments (e.g., video segments), wherein a data quality is determined in real-time for each segment (e.g., substantially immediately after the segment is acquired), and wherein a high quality PG dataset is generated contemporaneously with acquiring the data segments and/or contemporaneously with determining the data quality for the data segments (e.g., accumulating data segments to form the high quality PG dataset as each segment is validated). Different data segments can overlap (e.g., share data, be from overlapping timestamps) or be distinct.

Acquiring data S100 functions to acquire one or more datasets that can be used to determine a dataset quality (e.g., in S200), determine cardiovascular parameters (e.g., in S400), and/or can otherwise be used. S100 can be performed in response to a request, after (e.g., in response to) a user placing a body region on a sensor, after or during calibration, and/or at any other time. S100 is preferably performed using one or more sensors (e.g., to acquire the data), but can be performed by a computing system (e.g., to retrieve one or more datasets from a storage module) and/or by any suitable component.

S100 can include acquiring motion datasets (e.g., datasets associated with and/or that can be used to determine a motion state of a user and/or user device), image datasets, information extracted from image datasets (e.g., image attributes, image features, etc.), PG datasets (e.g., datasets associated with an arterial pressure), environmental datasets (e.g., datasets associated with an environmental property such as ambient light), and/or acquiring any suitable datasets. The PG datasets preferably include and/or are derived from an image set of a body region of a user (e.g., PG datasets can be features or attributes extracted from an image set acquired with a body region of the user in contact with the image sensor and/or optics thereof), but can additionally or alternatively include or be derived from a blood pressure sensor (e.g., blood pressure cuff, sphygmomanometer, etc.), plethysmogram sensor, and/or any suitable data source.

When more than one dataset is acquired, the datasets are preferably acquired contemporaneously and/or simultaneously (e.g., concurrently). However, the datasets can be acquired asynchronously, offline, delayed, and/or with any suitable timing.

Each dataset is preferably continuously acquired (e.g., for the duration of the method, until sufficient data is collected, until a trigger indicating that data acquisition can end, until a data quality changes, until a data quality changes by a threshold amount, until a user ends the data acquisition, until an API or application performing or hosting the method indicates an ending, until a user removes the body region from the sensor, etc.), but can be acquired intermittently, at predetermined times or frequency, at discrete times, and/or with any suitable timing.

Each dataset preferably corresponds to a time window that is at least a threshold number of seconds, but can alternatively be associated with any number of seconds and/or not be associated with a time window. The threshold number of seconds can be between 1 s-600 s or any range or value therebetween (e.g., 2 s, 4 s, 5 s, 8 s, 10 s, 12 s, 15 s, 20 s, 25 s, 50 s, 100s, etc.), but can alternatively be less than is or greater than 600 s. The time window can be a running time window, sliding time window, discrete time windows, and/or any suitable time window. The dataset can be contiguous or noncontiguous. The dataset can optionally be a data segment corresponding to the time window (e.g., within a larger time range), wherein multiple data segments can optionally be aggregated (e.g., via S300 methods).

S100 can include processing the datasets. For example, processing the datasets can be performed in and/or include the same or different steps as processing the datasets as discussed below in S300. However, the datasets can be processed in any manner.

S100 can include storing the dataset(s) (e.g., using the storage module). The dataset(s) can be stored indefinitely, for a predetermined amount of time, until a condition is met (e.g., until a data quality has been evaluated, until a cardiovascular parameter has been calculated, until a threshold amount of data with a target quality has been acquired, until attributes or features have been extracted, etc.). Datasets can be stored based on their quality, based on the data type, based on data completeness, and/or based on any suitable criteria. For example, only datasets with a high quality (e.g., meeting a criterion such as a good classification) can be stored. In an illustrative example of storing a dataset, an image buffer is generated while the image sensor is acquiring a video, wherein memory is temporarily allocated for each video frame (e.g., including relevant metadata, wherein metadata can include timestamps, resolutions, etc.). The video frames can then be provided to the data quality module for processing and/or analysis, wherein the image buffer is released back to the image sensor once each video frame's image buffer has been processed by the data quality module (e.g., transformed into luma and chroma values, image features extracted, etc.). However, all datasets can be stored and/or any suitable datasets can be stored based on any suitable criteria.

Determining a quality of the data S200 preferably functions to determine (e.g., assess, evaluate, etc.) a quality of dataset (e.g., acquired in S100). The quality is preferably used to determine whether a dataset can be used to determine a cardiovascular parameter (e.g., in S400, to achieve a target accuracy, to achieve a minimum accuracy, to achieve a target precision, to achieve a minimum precision, etc.), but can additionally or alternatively be used to determine whether to stop or continue data acquisition, and/or can otherwise be used. The quality is preferably a binary classification (e.g., 'good' vs 'bad', 'acceptable' vs 'unacceptable', etc.), but can be a continuous value, a nonbinary classification, and/or have any suitable format. S200 can be performed by a data quality module (e.g., of a local or remote computing system) and/or by any suitable component.

S200 is preferably performed on data acquired in S100, but can be performed on any suitable data. S200 is preferably performed on data segments corresponding to time windows, but can be performed on any suitable data. The time windows are preferably smaller than the time windows used to determine the cardiovascular parameter (e.g., in S400) and/or used to process the data (e.g., in S300), but can be the same size as and/or longer than the processed data windows. For example, the length of the data quality time windows can be between 0.5 s-600 s or any range or value therebetween (e.g., 0.5 s, is, 2 s, 4 s, 5 s, 8 s, 10 s, 12 s, 15 s, 20 s, 25 s, 50 s, 100 s, etc.), but can alternatively be less than 0.5 s or greater than 600 s. The time window can be a running time window, sliding time window, discrete time windows, and/or any suitable time window. The time window (e.g., and the corresponding number of frames in the corresponding data segment) is preferably predetermined, but can alternatively be empirically determined (e.g., how long a human can remain still) and/or otherwise determined (e.g., using ablation analysis to determine the minimum number of frames to accurately determine data quality).

S200 can be performed in parallel or series for different time windows. In an illustrative example, when 10 s of data are desirable for processing or determining a cardiovascular parameter, five (or more) instances of S200 can be performed simultaneously on 2 s segments of the data. In a second illustrative example, as data is acquired (e.g., as new time windows are populated with data), a data quality can be evaluated (e.g., for each 2 s segment of data). In a third illustrative example, a subsequent S200 iteration can be performed (e.g., on a new time window) after a prior S200 iteration (e.g., on a previous time window) failed to produce acceptable quality data. However, S200 can be performed for any suitable time windows and/or with any suitable timing.

S200 can be performed using one or more models (e.g., models in the data quality module). The models can use one or more of: machine learning (e.g., deep learning, neural network, convolutional neural network, etc.), statistical analysis, regressions, decision trees, thresholding, classification, rules, heuristics, equations (e.g., weighted equations, etc.), selection (e.g., from a library), instance-based methods (e.g., nearest neighbor), regularization methods (e.g., ridge regression), Bayesian methods (e.g., Naïve Bayes, Markov), kernel methods, probability, deterministics, genetic programs, support vectors, and/or leverage any suitable algorithms or methods to assess the data quality.

In a specific example, S200 can be performed using a motion model, a body region contact model, and/or a placement model. When a plurality of models is used, each model can be associated with an aspect of the data quality, a data type, an amount of data (e.g., time window duration, sensor reading frequency, etc.), a data quality (e.g., a first model can be used to determine whether data achieves a first quality and a second model can be used to determine whether data achieves a second quality, where the first and second model can use the same or different inputs), and/or can be associated with any suitable data or information.

In a first variant, S200 includes using a motion model to output a data quality. Data acquired via S100 (e.g., raw, aggregated, processed, features extracted from the data, attributes extracted from the data, etc.) can be inputted to the motion model, wherein the motion model outputs a classification. For example, the data can be user device motion sensor data (e.g., gyroscope, accelerometer, and/or gravity vector data). In a first embodiment, the classification can be based on a set of thresholds (e.g., an acceptable motion classification when all thresholds or other conditions are met, an unacceptable motion classification when one or more thresholds or other conditions are not met). In a second embodiment, the classification can be determined (e.g., predicted) by a model trained to predict an acceptable/unacceptable classification based on training data (e.g., sensor data labeled with acceptable/unacceptable classifications).

In a second variant, S200 includes using a body region contact model to output a data quality. Data acquired via S100 (e.g., raw, aggregated, processed, features extracted from the data, attributes extracted from the data, etc.) can be inputted to the body region contact model, wherein the body region contact model outputs a classification. For example, the data acquired via S100 can be a set of images (e.g., a data sample corresponding to a segment of a video), wherein image attributes can be extracted from the set of images and used as inputs for body region contact model. In examples, the image attributes can include total chroma for one or more channels (e.g., total chroma for each of red, blue, and green channels; total chroma for only red and blue channels, etc.), total luminance, and/or any other image attribute. The image attributes can be optionally aggregated across the set of images (e.g., an array of one or more image attribute values for each image; a single value for each image attribute corresponding to the entire set of images; etc.). In a first embodiment, the data quality output (e.g., a classification) is based on set of thresholds (e.g., predetermined thresholds corresponding to acceptable body region contact conditions). In a second embodiment, the data quality output is determined (e.g., predicted) by a body region contact model trained to predict 'body region detected' (e.g., associated with one or more acceptable body region contact conditions) or 'body region not detected' (e.g., associated with one or more unacceptable body region contact conditions) based on training data including image sets and/or aggregated image attributes labeled with 'body region detected' or 'body region not detected' (e.g., via S500 methods).

In a third variant, S200 includes using a placement model to output a data quality. Data acquired via S100 (e.g., raw, aggregated, processed, features extracted from the data, attributes extracted from the data, etc.) can be inputted to the placement model, wherein the placement model outputs a classification. For example, the data acquired via S100 can be a set of images, wherein image attributes can be extracted from the set of images and used as inputs for placement model. The set of images can the same set of images or a different set of images as used for the body region contact model. In an example, the image attributes can include luminance (and/or any other channel) summed across one or more image subregions (e.g., aggregate luminance for each row, aggregate luminance for each column, etc.). The image attributes can be optionally aggregated across the set of images (e.g., an array of one or more image attribute values for each image; a single value for each image attribute corresponding to the entire set of images; etc.). In a first embodiment, the data quality output (e.g., a classification) is based on set of thresholds (e.g., predetermined thresholds corresponding to acceptable body region placement conditions). For example, each image subregion can optionally have a different threshold. In a second embodiment, the data quality output is determined (e.g., predicted) by a placement model trained to predict 'acceptable body region placement' (e.g., associated with one or more acceptable body region placement conditions) or 'unacceptable body region placement' (e.g., associated with one or more unacceptable body region placement conditions) based on training data including image sets and/or aggregated image attributes labeled with 'acceptable body region placement' or 'unacceptable body region placement' (e.g., via S500 methods). Alternatively, the data quality output is determined by a placement model trained to predict a guidance label (e.g., 'acceptable finger placement', 'finger pressure too high', 'finger pressure too low', 'finger too far down', 'finger too far up', 'finger too far left', 'finger too far right', 'finger motion too high', etc.) based on training data labeled with the guidance labels.

Figure 9:
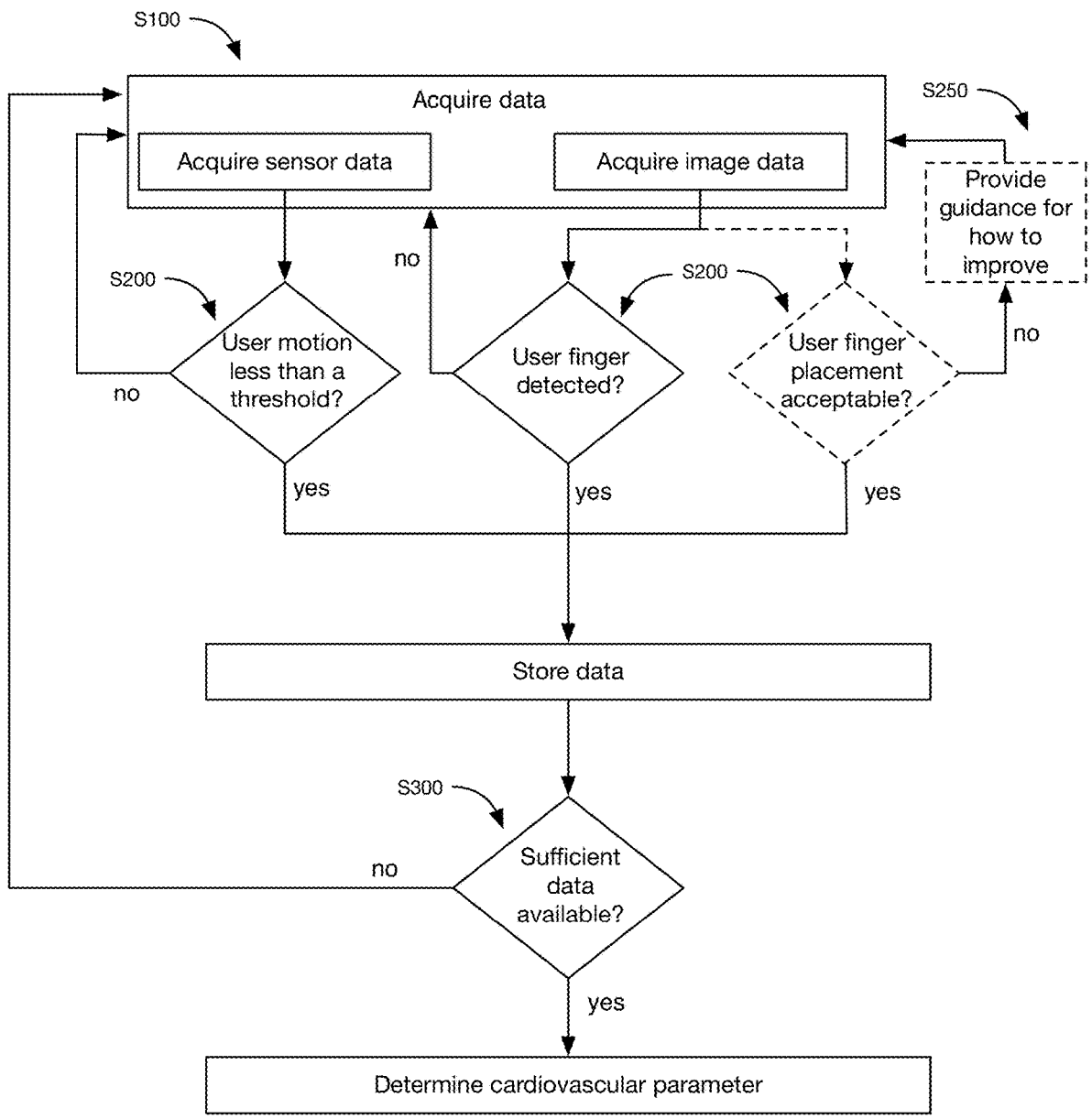
FIG. 9 depicts a first example of determining a cardiovascular parameter.
Figure 10:
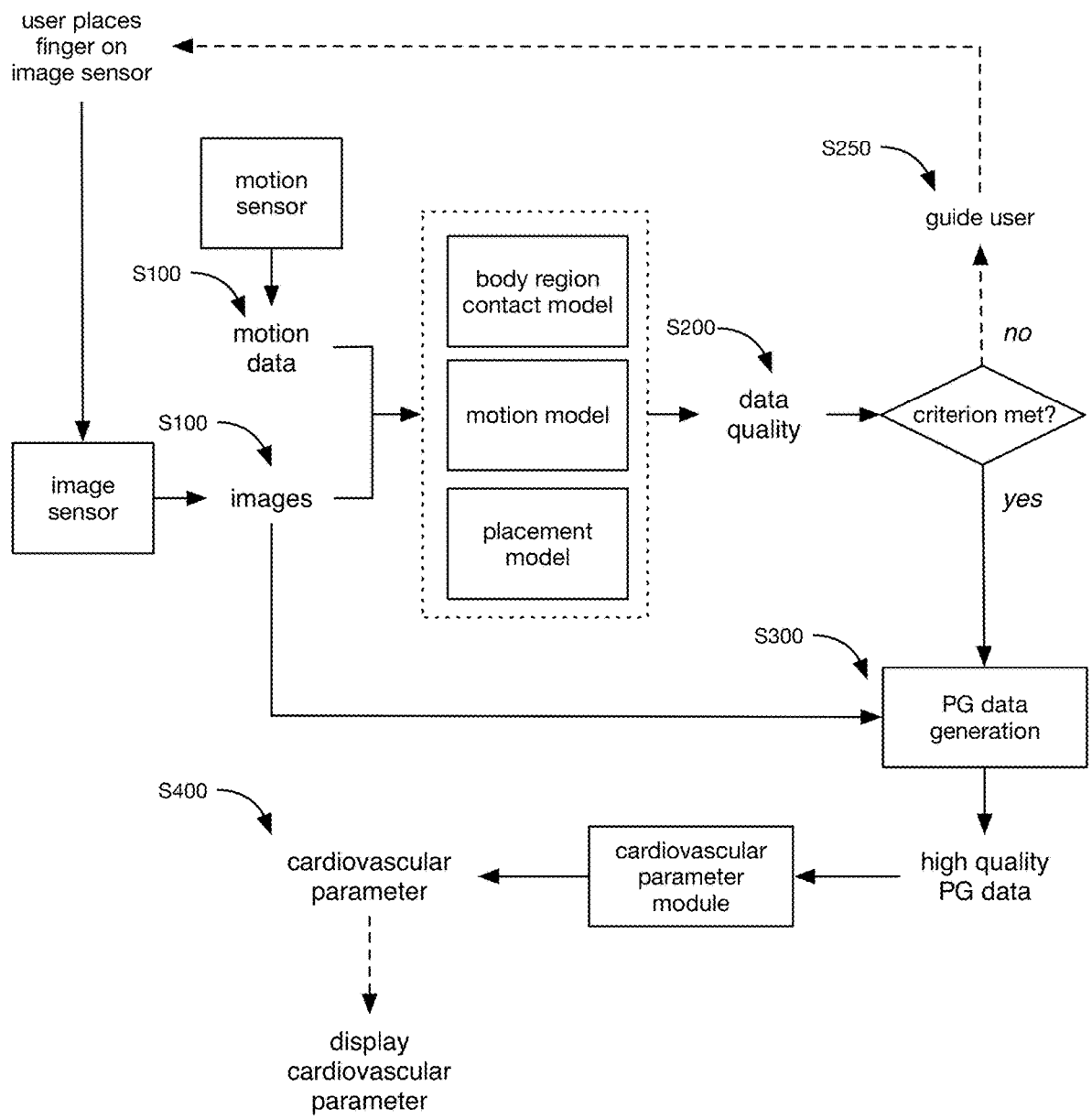
FIG. 10 depicts a second example of determining a cardiovascular parameter.

When a plurality of models is used, the data quality can be determined by consensus between models, by voting, as a weighted value (e.g., score), as a probability (e.g., by combining probabilities), using a combining model (e.g., a model that takes the outputs from the previous models and outputs a data quality), using a logical operator, according to a prioritization, and/or can otherwise be determined from the plurality of models (e.g., as described for the data quality module). For example, when any of the models outputs a poor data quality (e.g., a bad classification, an unacceptable classification, a quality less than a threshold, etc.), the data can be poor quality (e.g., example shown in FIG. 9). In a first example, each model is evaluated in series. In this example, when one model outputs a poor data quality, the overall data quality can optionally be classified as poor data quality without evaluating the later models in the series (e.g., which can preserve computational resources). In a second example, each model is evaluated in parallel. However, a data quality can otherwise be determined.

High quality data (e.g., a data quality meeting one or more criteria such as: a 'good' or acceptable classification, a score that is at least a threshold, a probability of acceptable cardiovascular parameter calculation exceeds a threshold, etc.) is preferably stored and/or used to determine the cardiovascular parameter (e.g., in S300 or S400 such as after enough high quality data has been acquired). When low (or high) quality data (e.g., 'bad' or 'unacceptable' classification, a score that is at most a threshold, a probability of acceptable cardiovascular parameter calculation is at most a threshold, etc.) is detected (e.g., identified, labeled, etc.), S100 can be performed again (e.g., restarted), high quality data within a threshold distance (e.g., time) of the low quality data can be excluded (e.g., from S300, from S400, from storage, etc.), data can be processed to improve a quality (e.g., using a transformation that converts the data to a higher data quality), a flag can be issued indicating a data quality (e.g., to be attached, appended, or otherwise associated with a cardiovascular parameter determined using the dataset), instructions (e.g., advice or feedback) for improving data quality can be generated and/or presented to the user (and/or operator), and/or any suitable response can occur.

However, a data can be used in any manner based on a data quality comparison to one or more criteria.

The method can optionally include guiding a user based on the quality of the data S250 which can function to instruct the user to adjust one or more conditions based on the data quality (e.g., based on an output of the data quality module). Conditions can include: a user, user device, and/or user body region motion; a body region pose relative to a sensor; body region contact pressure; environmental conditions (e.g., ambient light); and/or any other parameter affecting data quality. The user is preferably guided on the user device, but can alternatively be guided on any other suitable system.

The user can be guided based on a data quality using: look-up models, decision trees, rules, heuristics, selection methods, machine learning, regressions, thresholding, classification, equations, probability or other statistical methods, deterministics, genetic programs, support vectors, instance-based methods, regularization methods, Bayesian methods, kernel methods, and/or any other suitable method. In an example, each data quality output from one or more models (e.g., the placement model) in the data quality module is mapped to a user guidance. In an illustrative example, a placement model output of [1,0,0,0,0,0,0,0] results in no guidance (e.g., acceptable body region placement); [0,1,0, 0,0,0,0,0] results in 'lower body region contact pressure' guidance; [0,0,1,0,0,0,0,0] results in 'increase body region contact pressure' guidance; [0,0,0,1,0,0,0,0] results in 'move body region up' guidance; [0,0,0,0,1,0,0,0] results in 'move body region down' guidance; [0,0,0,0,0,1,0,0] results in 'move body region left' guidance; [0,0,0,0,0,0,1,0] results in 'move body region right' guidance; [0,0,0,0,0,0,0,1] results in 'stop moving body region' guidance.

In a first variant, the user can be instructed to decrease motion of the user device in response to a flag outputted from the motion model (e.g., indicating unacceptable conditions). An example is shown in FIG. 17A. In a second variant, the user can be instructed to improve body region contact with the sensor in response to a flag outputted from the body region contact model (e.g., indicating unacceptable conditions). In examples, the user can be instructed to: place the body region on the sensor, adjust positioning of the body region on the sensor, adjust contact pressure, increase blood flow to the body region (e.g., by making a fist), and/or perform any other adjustment. An example is shown in FIG. 17B. In a third variant, the user can be instructed to improve body region placement relative to the sensor (e.g., including pose and/or contact pressure) in response to a flag outputted from the placement model (e.g., indicating unacceptable conditions). In a first example, the user can be instructed to move the body region in a direction (e.g., up, down, left, or right), wherein the direction is based on the placement model output. In an illustrative example, the user is instructed to move their finger to the left when the placement model output indicates the finger is too far to the right of the camera lens center. In a second example, the user can be instructed to adjust contact pressure of the body region on the sensor, wherein the pressure adjustment (e.g., increase vs decrease, the amount of adjustment, etc.) is based on the placement model output. In a fourth variant, different combinations of data quality module outputs (e.g., classifications) map to different guidance. Additionally or alternatively, a flag from one or more data quality modules can result in discarding the corresponding data sample (e.g., a video acquired via S100 and analyzed via S200) and restarting data acquisition (e.g., all or parts S100), wherein the user can optionally be informed that data acquisition is restarting.

Figure 16A:
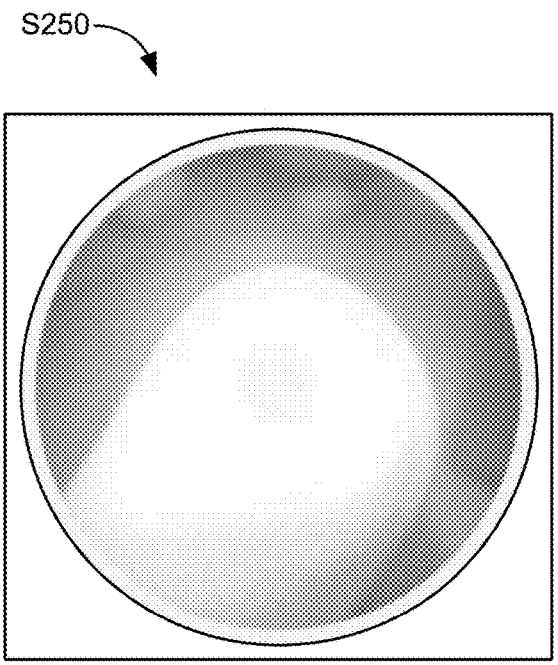
FIGS. 16A and 16B depict illustrative examples of using a live video to guide a user.
Figure 16B:
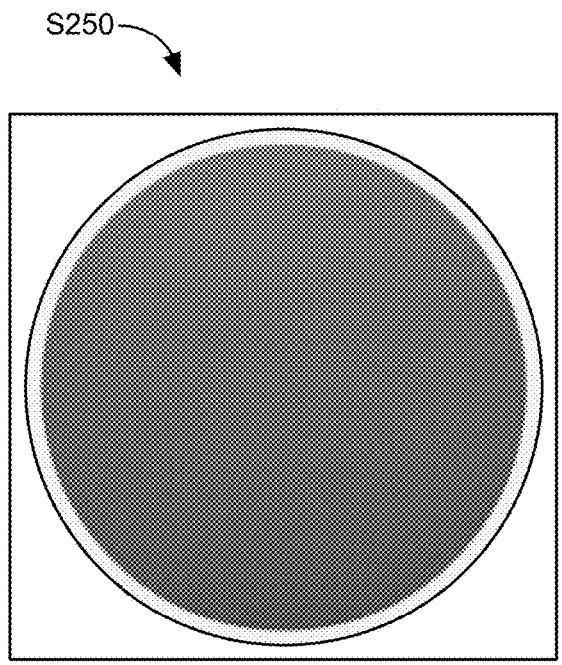

Additionally or alternatively, the user can be guided using a video (e.g., live video) of the body region of the user. An example is shown in FIG. 16A and FIG. 16B.

Additionally or alternatively, S250 can be performed during S100. For example, the user can be guided while acquiring data (e.g., image data, motion data, etc.) to vary a set of conditions (e.g., contact pressure, body region pose including position and/or orientation, user device pose, environmental parameters, etc.). The data quality can be assessed in each of the set of conditions to determine at least one condition associated with data of desired quality. The set of conditions can be a predetermined set of conditions, such that the individual is guided to sequentially vary the conditions; however, the set of conditions can alternatively not be predetermined, such that the individual is able to freely adjust the conditions. S250 can additionally or alternatively include guiding the user to maintain the condition that results in the best data quality.

However, the user can be otherwise guided.

Processing the datasets S300 preferably functions to format and/or analyze the dataset(s) (e.g., to facilitate or enable their use in S400 and/or S500). S300 can be performed by a processing module (e.g., of a local or remote computing system), and/or by any suitable component. S300 can be performed after S100 (e.g., after each segment of data is acquired), after S200 (e.g., after data quality is determined for each segment of data), and/or at any other time. The datasets processed in S300 are preferably data used in (e.g., validated in) S200, but can alternatively be a subset of data used in S200, a superset of data used in S200, and/or entirely different from data used in S200. S300 preferably processes data with high quality (e.g., 'good' data), but can process low quality, data without a quality, and/or any suitable quality data.

Examples of processing the datasets can include: aggregating datasets; removing outliers, averaging (e.g., using a moving average) the datasets, converting an image set to PG data (e.g., by averaging or summing intensity of images of the image set, using a transformation, otherwise generating a PG dataset, etc.), resampling the datasets; filtering the datasets; segmenting the datasets; denoising the datasets; determining a subset of the datasets to analyze; and/or otherwise processing the datasets.

S300 preferably processes at least a threshold number of seconds worth of data, but can alternatively process any number of seconds worth of data and/or process data not associated with a time window. The threshold number of seconds (e.g., prior to aggregating datasets) can be between 0.5 s-600 s or any range or value therebetween (e.g., 0.5 s, 1 s, 2 s, 4 s, 5 s, 8 s, 10 s, 12 s, 15 s, 20 s, 25 s, 50 s, 100 s, etc.), but can alternatively be less than 0.5 s or greater than 600 s. Aggregating datasets can optionally include accumulating data segments to generate a threshold amount of data (e.g., a threshold number of seconds worth of data). The threshold number of seconds can be between 4 s-600 s or any range or value therebetween (e.g., 5 s, 8 s, 10 s, 12 s, 15 s, 20 s, 25 s, 50 s, 100 s, etc.), but can alternatively be less than 4 s or greater than 600 s. The data (e.g., aggregated data) can be contiguous (e.g., PG data extracted from an uninterrupted segment of a video) or noncontiguous (e.g., PG data extracted from discrete, non-neighboring segments of a video).

Figure 8:
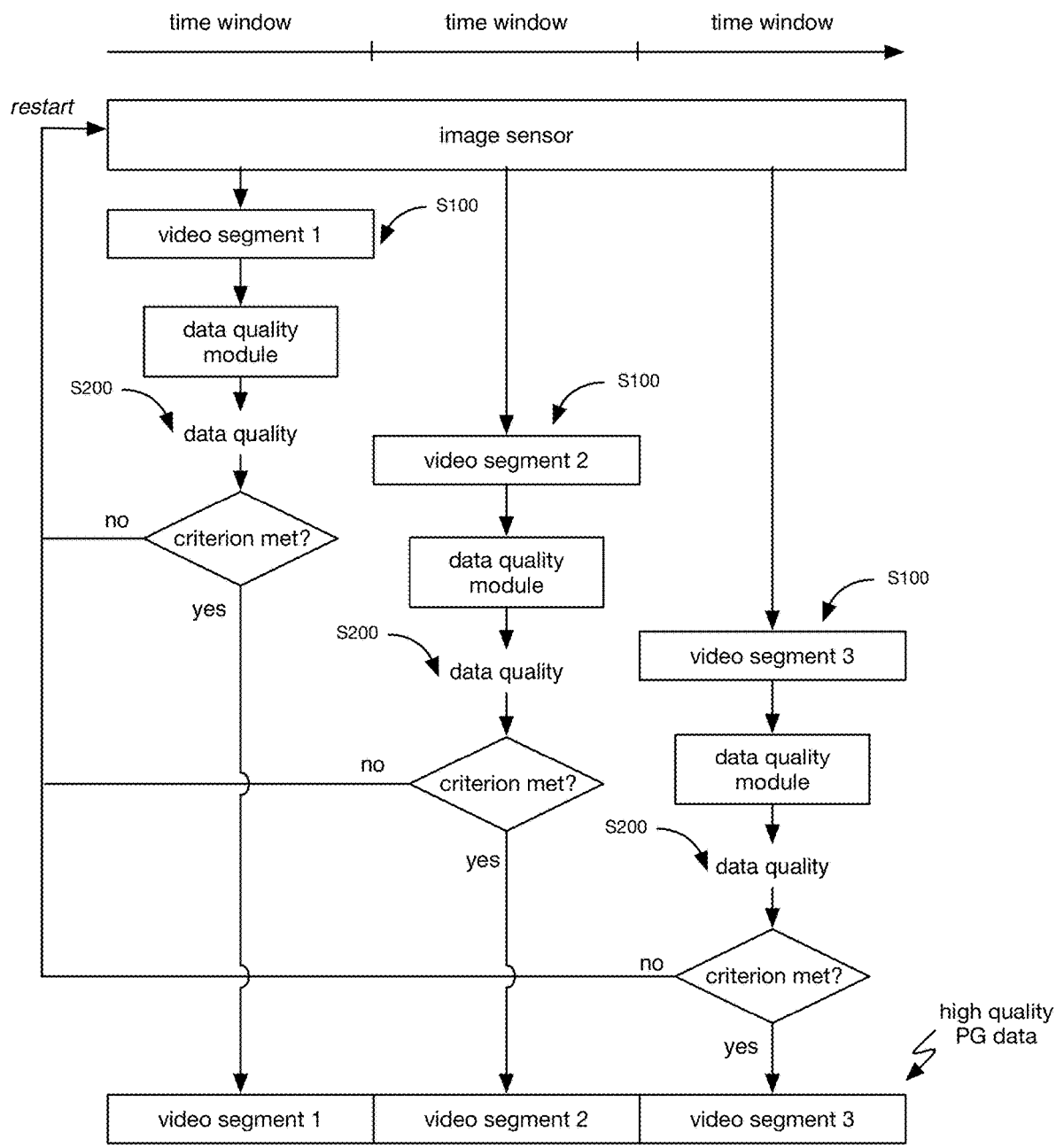
FIG. 8 depicts an example of generating a high quality plethysmogram (PG) dataset.
Figure 12:
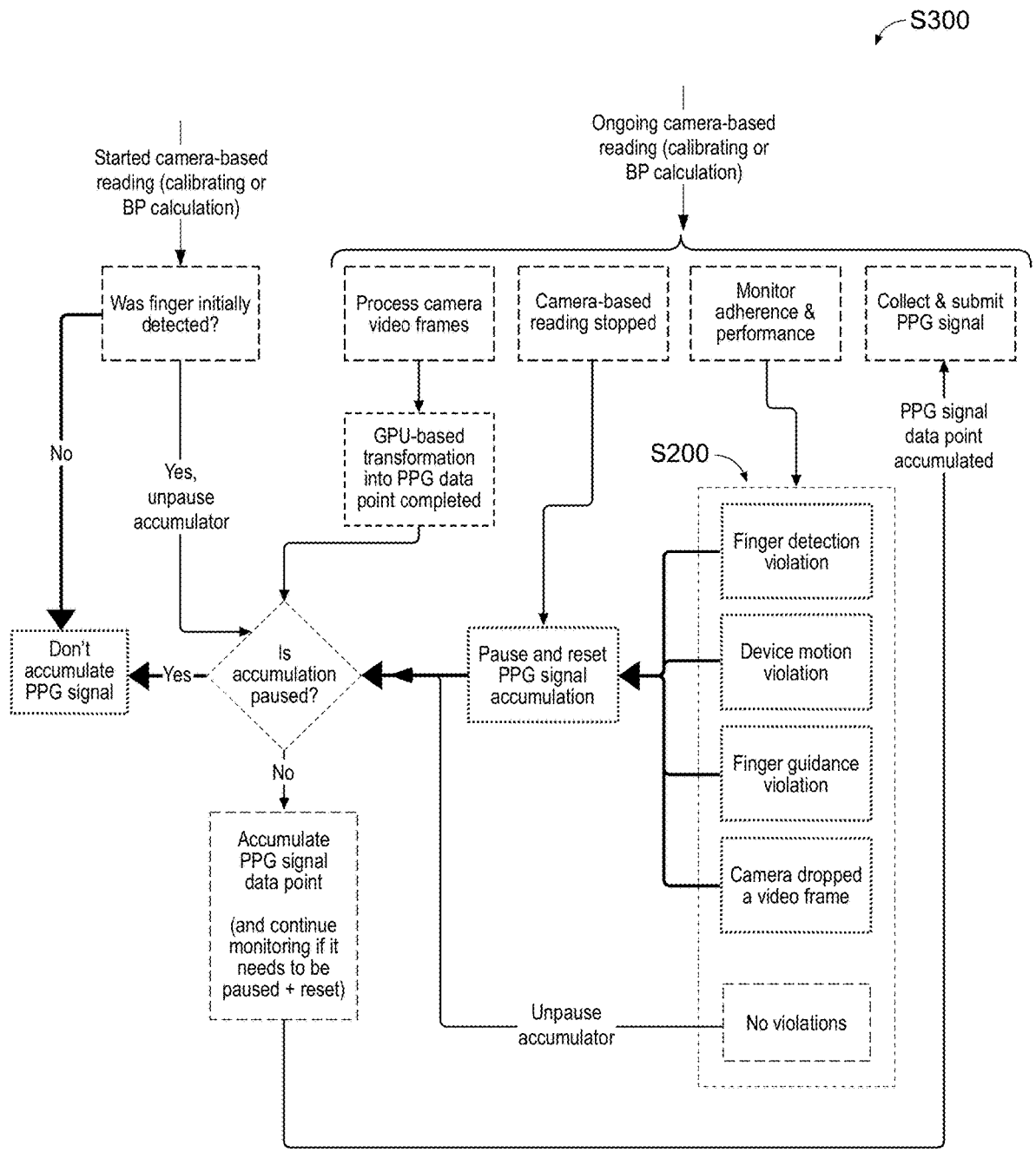
FIG. 12 depicts an illustrative example of accumulating data segments.

In an example of aggregating datasets, consecutive or nonconsecutive segments of data can be accumulated to generate a timeseries of aggregated data, wherein the length of the timeseries of aggregated data can be substantially equal to the threshold length of time (e.g., as described for data inputs to the cardiovascular parameter module). In an illustrative example, a first segment of data is acquired (e.g., a first video) via S100 methods, wherein data quality associated with the first segment is classified via S200 methods. If the data quality classification is 'bad', the first segment is discarded and data accumulation restarts. If the data quality classification is 'good', a second segment of data is acquired (e.g., a second video, consecutive with the first video) via S100 methods, wherein data quality associated with the second segment is classified via. S200 methods. If the data quality classification associated with the second segment is 'good', the second segment is appended to the first segment to generate an aggregated timeseries. If the data quality classification associated with the second segment is 'bad', either: both segments of data can be discarded and data accumulation restarts (e.g., such that the final aggregated timeseries is contiguous); or only the second segment is discarded and the data accumulation method resumes for a new second segment (e.g., such that the final aggregated timeseries is noncontiguous). Subsequent segments can be iteratively appended until the aggregated timeseries reaches a threshold length of time. Examples are shown in FIG. 8 and FIG. 12.

Processing the datasets can be performed, in a first example, in a manner as disclosed in U.S. patent application Ser. No. 17/761,152 titled 'METHOD AND SYSTEM FOR DETERMINING CARDIOVASCULAR PARAMETERS' filed on 16 Mar. 2022 which is incorporated in its entirety by this reference. Processing the datasets can be performed, in a second example, as disclosed in U.S. patent application Ser. No. 17/866,185 titled 'METHOD AND SYSTEM FOR CARDIOVASCULAR DISEASE ASSESSMENT AND MANAGEMENT' filed on 15 Jul. 2022 which is incorporated in its entirety by this reference. However, processing the datasets can be performed in any manner.

Determining the cardiovascular parameter(s) S400 functions to evaluate, calculate, estimate, and/or otherwise determine the user's cardiovascular parameters from the PG dataset (e.g., processed PG dataset, denoised PG dataset, segmented PG dataset, filtered PG dataset, interpolated PG dataset, raw PG dataset, etc.). S400 can additionally or alternatively function to determine fiducials (and/or any other suitable parameters) associated with the cardiovascular parameters of the individual. The user's cardiovascular parameters are preferably determined using high quality datasets (e.g., high quality PG data), but can be determined using low quality datasets (e.g., with or without reporting an estimated error from using lower quality data, with or without including a flag indicating that potentially faulty data has been used, etc.), using a combination of high and low quality datasets, and/or using any suitable data. S400 is preferably performed using a cardiovascular parameter module (e.g., of a computing system such as a local or remote computing system), but can be performed by any suitable component. The PG dataset is preferably transformed (e.g., using a linear transformation, using a nonlinear transformation, etc.) into the cardiovascular parameter. However, additionally, or alternatively, any suitable dataset can be used (e.g., used to calculate) and/or transformed into the cardiovascular parameter.

Determining the cardiovascular parameter can include analyzing the PG dataset (e.g., an analysis PG dataset). The PG dataset can be analyzed on a per segment basis (e.g., cardiovascular parameters determined for each segment), for the PG dataset as a whole, for an averaged PG dataset, and/or otherwise be analyzed. S400 is preferably performed independently for each segment of the PG dataset; however, S400 can be performed for the entire PG dataset, the analysis of one segment can depend on the results of other segments, and/or any suitable subset of the PG dataset can be analyzed.

The cardiovascular parameter(s) can be determined based on the PG dataset, fiducials, and/or cardiovascular manifold using regression modeling (e.g., linear regression, nonlinear regression, generalized linear model, generalized additive model, etc.), learning (e.g., a trained neural network, a machine-learning algorithm, etc.), an equation, a look-up table, conditional statements, a transformation (e.g., a linear transformation, a non-linear transformation, etc.), and/or determined in any suitable manner.

The transformation (e.g., correlation) between the fiducials and/or the cardiovascular manifold and the cardiovascular parameters is preferably determined based on a calibration dataset (e.g., a calibration dataset such as from a blood pressure cuff, ECG measurements, etc. generated at approximately the same time as the analysis PG dataset; a second PG dataset such as at a different body region of the individual, of a different individual, of the individual in a different activity state, etc.; a calibration dataset including an analysis PG dataset for each individual of a control group with a corresponding measured cardiovascular parameter; etc.); however, the transformation can be determined from a model (e.g., a model of the individual's cardiovascular system, a global model such as one that can apply for any user, etc.), and/or determined in any suitable manner.

In variants, S400 can include: determining fiducials; determining cardiovascular parameters; and storing the cardiovascular parameters. However, S400 can include any suitable processes.

Determining fiducials preferably functions to determine fiducials for the PG dataset (e.g., processed dataset, denoised dataset, segmented dataset, filtered dataset, interpolated dataset, raw dataset, etc.). This preferably occurs before determining the cardiovascular parameters; however, the fiducials can be determined at the same time as and/or after cardiovascular parameter determination. The set of fiducials can depend on the cardiovascular parameters, characteristics of the individual, a supplemental dataset, and/or any suitable information. In some variants, different fiducials can be used for different cardiovascular parameters; however, two or more cardiovascular parameters can be determined from the same set of fiducials.

In a first variant, determining the fiducials can include decomposing the PG dataset (e.g., for each segment in the analysis PG dataset) into any suitable basis function(s). In a specific example, decomposing the PG dataset can include performing a discrete Fourier transform, fast Fourier transform, discrete cosine transform, Hankel transform, polynomial decomposition, Rayleigh, wavelet, and/or any suitable decomposition and/or transformation on the PG dataset. The fiducials can be one or more of the decomposition weights, phases, and/or any suitable output(s) of the decomposition. However, the fiducials can be determined from the PG dataset in any suitable manner.

In a second variant, determining the fiducials can include fitting the PG dataset to a predetermined functional form. The functional form can include radial basis functions (e.g., gaussians), Lorentzians, exponentials, super-gaussians, Lévy distributions, hyperbolic secants, polynomials, convolutions, linear and/or nonlinear combinations of functions, and/or any suitable function(s). The fitting can be constrained or unconstrained. In a first specific example, a linear combination of 5 constrained gaussians (e.g., based on user's cardiovascular state and/or phase) can be used to fit each segment of the PG data. In a second specific example, a linear combination of 4 gaussians can be fit to each segment of the PG data. The 4 gaussians can represent: a direct arterial pressure model, two reflected arterial pressure models, and a background model (e.g., where the background is a slow moving gaussian for error correction). However, any other number of gaussians, representing any other suitable biological parameter, can be fit (e.g., concurrently or serially) to one or more segments of the PG data.

The functional form can be fit to the PG dataset based on: a loss between the functional form and the PG dataset, a loss between derivatives of the functional form and derivatives of the PG dataset (e.g., first derivative, second derivative, third derivative, a weighted combination of derivatives, etc.), and/or any other fitting methods. In an illustrative example, a linear combination of gaussians are simultaneously fit to a segment of the PG data to minimize loss between the first, second, and third derivative of the linear combination of gaussians relative to the first, second, and third derivative of the PG data segment, respectively. The fitting can be multi-stage or single-stage. In a specific example of multi-stage fitting, the first fitting stage includes determining a timing parameter (e.g., spacing between gaussians, frequency, center position and/or any other model location, ordinal, etc.) of each gaussian in a linear combination of gaussians by minimizing loss between the first and/or second derivative of the linear combination of gaussians relative to the first and/or second derivatives of the PG data segment, respectively. The second fitting stage includes determining an amplitude parameter (e.g., the amplitude, a parameter in the gaussian function that influences the amplitude, a parameter based on the amplitude, etc.) of each gaussian in the linear combination by minimizing loss between the third derivative of the linear combination of gaussians relative to the third derivative of the PG data segment. In this second stage, the timing parameter for each gaussian can be substantially constrained.

However, any suitable fit can be performed.

Figure 19:
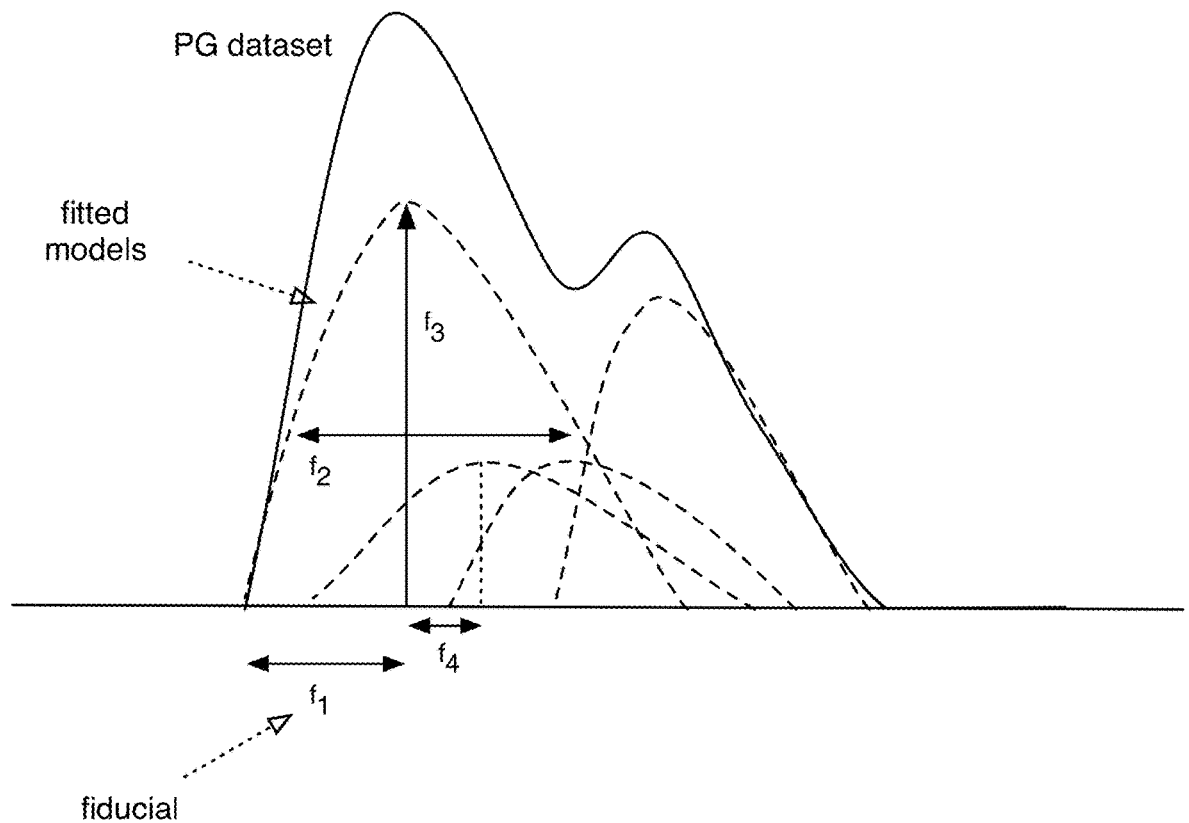
FIG. 19 is a schematic representation of examples of possible fiducials determined based on a functional form fit to a segment of the PG dataset.

In this variant, the fiducials are preferably one or more of the fit parameters (e.g., full width at half max (FWHM), center position, location, ordinal, amplitude, frequency, spacing, any timing parameter, any amplitude parameter, etc.); however, the fiducials can include statistical order information (e.g., mean, variance, skew, etc.) and/or any suitable information. An example is shown in FIG. 19.

Determining the cardiovascular parameters preferably functions to determine the cardiovascular state (e.g., set of cardiovascular parameter values) for the user. The cardiovascular parameters can be determined based on the fiducials (e.g., for a single segment; for the entire PG dataset, wherein corresponding fiducials are aggregated across the segments; etc.), based on the cardiovascular manifold, and/or otherwise be determined. This preferably determines cardiovascular parameters relating to each segment of the PG dataset (e.g., each heartbeat); however, this can determine a single cardiovascular parameter value for the entire PG dataset (e.g., a mean, variance, range, etc.), a single cardiovascular parameter, and/or any suitable information. This preferably occurs before storing the cardiovascular parameters; however, S436 can occur simultaneously with and/or after storing the cardiovascular parameters.

In a first variant, the cardiovascular parameters can be determined by applying a fiducial transformation to the set of fiducials. The fiducial transformation can be determined from a calibration dataset (e.g., wherein a set of fiducial transforms for different individuals are determined by multiplying the cardiovascular parameters by the inverse matrix of the respective fiducials), based on a model (e.g., a model of the individual, a model of human anatomy, a physical model, etc.), generated using machine learning (e.g., a neural network), generated from a manifold (e.g., relating fiducial value sets with cardiovascular parameter value sets), based on a fit (e.g., least squares fit, nonlinear least squares fit, generalized linear model, generalized additive model, etc.), and/or be otherwise determined. The fiducial transformation can be a universal transformation, be specific to a given cardiovascular parameter or combination thereof, be specific to the individual's parameters (e.g., age, demographic, comorbidities, biomarkers, medications, estimated or measured physiological state, etc.), be specific to the individual, be specific to the measurement context (e.g., time of day, ambient temperature, etc.), or be otherwise generic or specific. The fiducial transformation can be the average, median, most accurate (e.g., lowest residuals, lowest error, etc.), based on a subset of the control group (e.g., a subset of the control group with one or more characteristics similar to or matching the individual's characteristics), selected based on voting, selected by a neural network, randomly selected, and/or otherwise determined from the calibration dataset. The fiducial transformation can be normalized, wherein the fiducial values and/or the cardiovascular parameter values used to determine the transformation are demeaned and/or otherwise modified.

Figure 20:
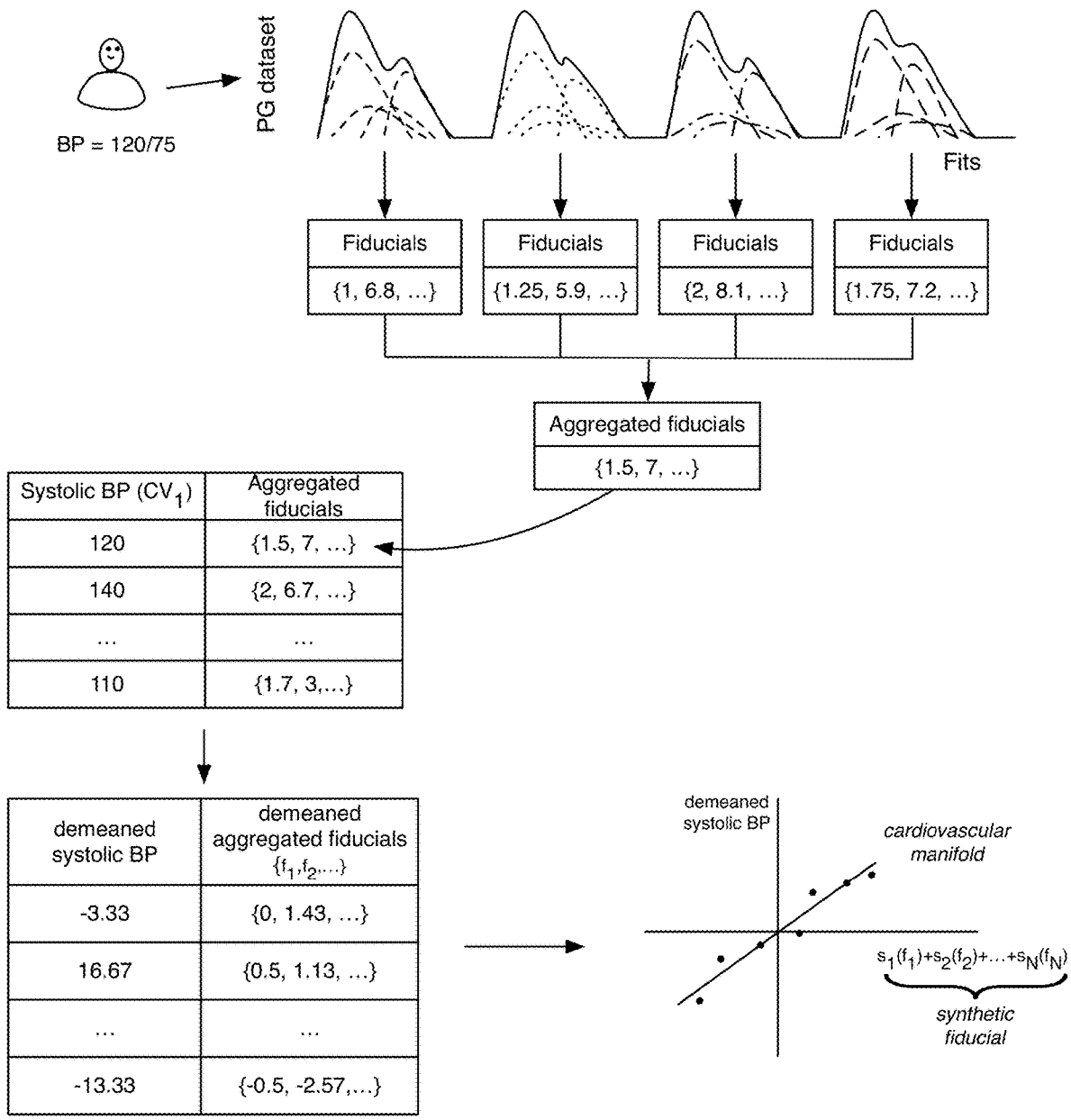
FIG. 20 is a schematic representation of an example of determining a linear cardiovascular manifold.

The fiducial transformation can be a linear or nonlinear transformation. In an example, the fiducial transformation is a linear transformation of a synthetic fiducial, wherein the synthetic fiducial is a combination (e.g., linear combination, nonlinear combination, etc.) of the set of fiducials. In this example, the transformation can be determined based on a generalized additive model fit to a calibration dataset including cardiovascular parameters and a set of fiducial values corresponding to each cardiovascular parameter (e.g., where the link function of the generalized additive model is the transformation of the synthetic fiducial, where the predictor of the generalized additive model is the synthetic fiducial). An example is shown in FIG. 20. In an illustrative example, determining cardiovascular parameters can include: calculating a synthetic fiducial from the set of fiducials (e.g., using a weighted sum of the fiducials, etc.); and determining a relationship (e.g., linear relationship) between the synthetic fiducial and the cardiovascular parameter. This can be used to determine the universal relationship, manifold, or model (e.g., reference relationship); an individual's relationship, manifold, or model; and/or any other relationship, manifold, or model. However, the fiducial transformation can be otherwise applied.

Each cardiovascular parameter can be associated with a different fiducial transformation and/or one or more cardiovascular parameters can be associated with the same fiducial transformation (e.g., two or more cardiovascular parameters can be correlated or covariate). In a specific example of the first variant, the cardiovascular parameters can be determined according to:

$$AT=B$$

where A corresponds to the set of fiducials, T corresponds to the fiducial transformation, and B corresponds to the cardiovascular parameter(s).

In a specific example, the method includes: determining the fiducial transformation for an individual, and determining the cardiovascular parameter value(s) for the individual based on a subsequent cardiovascular measurement and the fiducial transformation. The fiducial transformation is preferably determined from a set of calibration data sampled from the individual, which can include: fiducials extracted from calibration cardiovascular measurements (e.g., PG data, plethysmogram data) (A), and calibration cardiovascular parameter measurements (e.g., blood pressure, O2 levels, etc.; measurements of the cardiovascular parameter to be determined) (B). The fiducial transformation (T) for the individual is determined from AT=B. T is subsequently used to determine the cardiovascular parameter values for fiducials extracted from subsequently-sampled cardiovascular measurements.

In a second variant, the cardiovascular parameters can be determined based on where the individual is on the individual's cardiovascular manifold, a manifold transformation from the individual's cardiovascular manifold to a universal cardiovascular manifold, and optionally a mapping transformation from the individual's position on the universal cardiovascular manifold to the cardiovascular parameter values. The cardiovascular parameter can additionally or alternatively depend on a change in where the individual is on the cardiovascular manifold (e.g., a change in fiducial values, a change in a cardiovascular parameter, etc.), the individual's effective location on the universal cardiovascular manifold (e.g., a normalized universal cardiovascular manifold), the change in the individual's effective location on the universal cardiovascular manifold, and/or otherwise depend on the individual's relationship to the cardiovascular manifold. The universal cardiovascular manifold can be determined from the calibration dataset, determined from a model, generated using machine learning (e.g., a neural network), and/or be otherwise determined. The universal cardiovascular manifold can be an average of, include extrema of, be learned from (e.g., using machine learning algorithm to determine), be selected from, and/or otherwise be determined based on the calibration dataset. The universal cardiovascular manifold preferably maps values for one or more fiducials to values for cardiovascular parameters, but can be otherwise constructed. The universal cardiovascular manifold preferably encompasses at least a majority of the population's possible fiducial values and/or cardiovascular parameter values, but can encompass any other suitable swath of the population. The universal cardiovascular manifold can be specific to one or more cardiovascular parameters (e.g., the system can include different universal manifolds for blood pressure and oxygen levels), but can alternatively encompass multiple or all cardiovascular parameters of interest. The manifold transformation can include one or more affine transformation (e.g., any combination of one or more: translation, scaling, homothety, similarity transformation, reflection, rotation, and shear mapping) and/or any suitable transformation. In an illustrative example of the second variant, the individual's cardiovascular phase can be determined and aligning (e.g., using a transformation) the individual's cardiovascular phase to a universal cardiovascular phase (e.g., associated with a universal cardiovascular manifold), where a relationship between the universal cardiovascular phase and the cardiovascular parameters is known.

Figure 22:
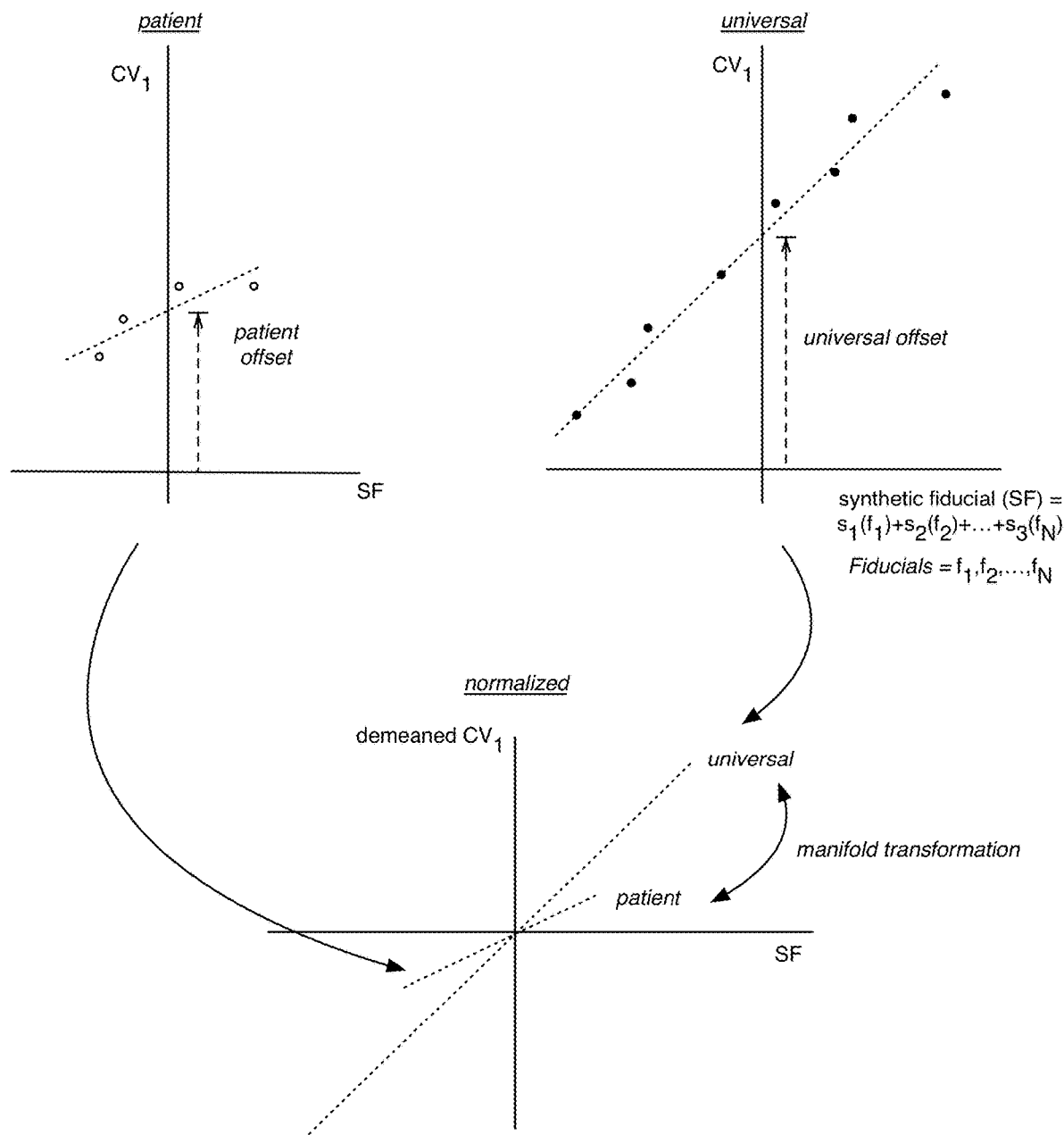
FIG. 22 is a schematic representation of an example of a transformation between cardiovascular manifolds.

In a first specific example, the method includes: generating the universal manifold from population calibration data, generating an individual manifold from an individual's calibration data, and determining a transformation between the individual manifold and the universal manifold. The universal manifold is preferably a finite domain and encompasses all (or a majority of) perturbations and corresponding cardiovascular parameter values (e.g., responses), but can encompass any other suitable space. The universal manifold preferably relates combinations of fiducials (with different values) with values for different cardiovascular parameters (e.g., relating one or more reference sets of fiducials and one or more reference cardiovascular parameters), but can relate other variables. The individual calibration data preferably includes cardiovascular measurements (e.g., PG data, plethysmogram data) corresponding to cardiovascular parameter measurements (e.g., blood pressure), but can include other data. The population calibration data preferably includes data similar to the individual calibration data, but across multiple individuals (E.g., in one or more physiological states). The transformation can be: calculated (e.g., as an equation, as constants, as a matrix, etc.), estimated, or otherwise determined. The transformation preferably represents a transformation between the individual and universal manifolds, but can additionally or alternatively represent a mapping of the fiducial position on the universal manifold (e.g., the specific set of fiducial values, transformed into the universal domain) to the cardiovascular parameter values (e.g., in the universal domain). Alternatively, the method can apply a second transformation, transforming the universal-transformed fiducial values to the cardiovascular parameter values (e.g., in the universal domain). The transformation(s) are subsequently applied to the fiducials extracted from subsequent cardiovascular measurements from the individual to determine the individual's cardiovascular parameter values. The transformation can optionally be between normalized manifolds, wherein a normalized manifold can include a relationship between cardiovascular parameters and fiducials determined based on demeaned cardiovascular parameters (e.g., subtracting a cardiovascular parameter offset, wherein the cardiovascular parameter offset is defined as the average of the cardiovascular parameters) and demeaned fiducials (e.g., wherein a fiducial offset is subtracted from the synthetic fiducials; wherein a fiducial offset is subtracted from values for each fiducial, etc.); an example is shown in FIG. 22.

Figure 21:
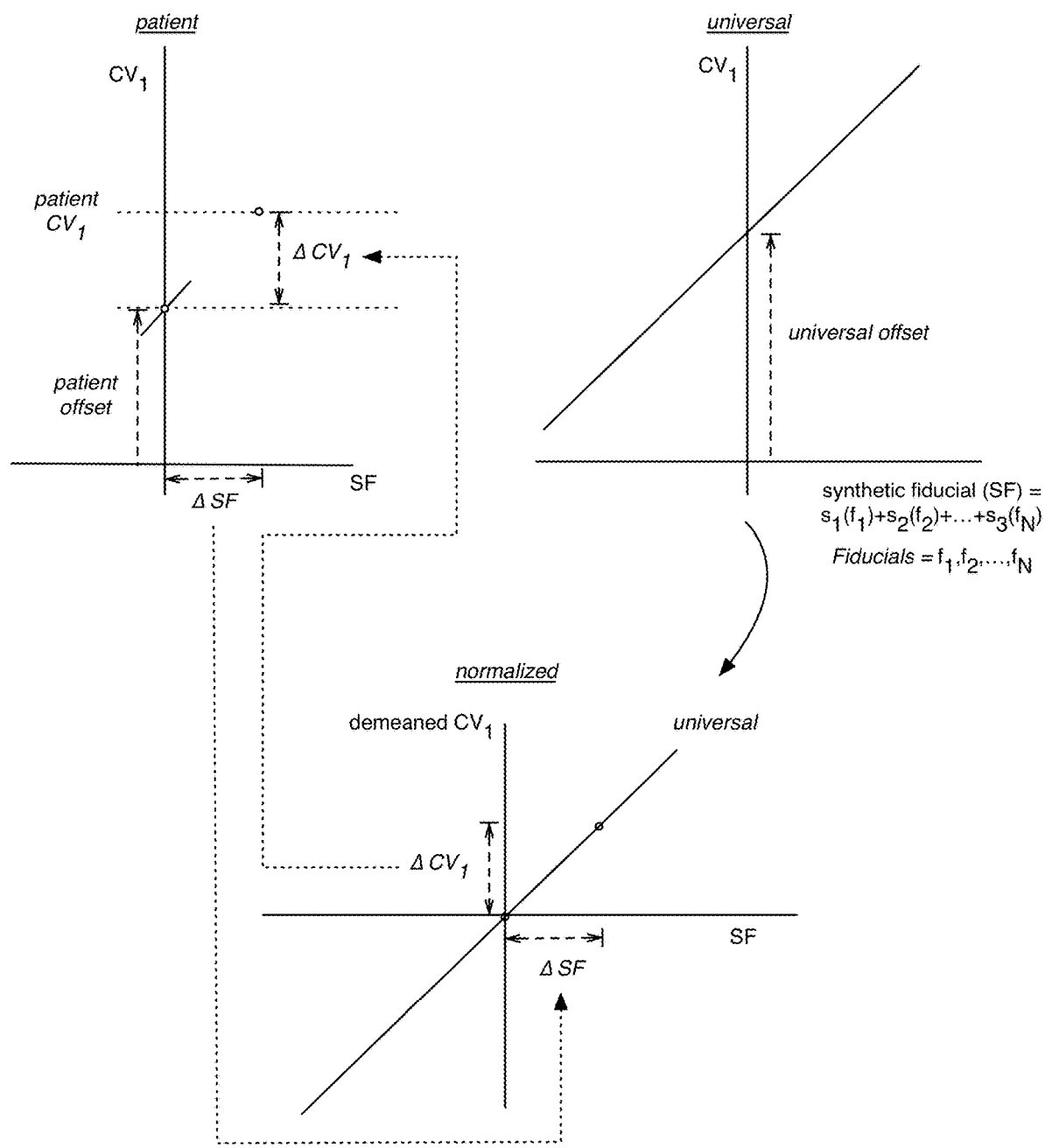
FIG. 21 is a schematic representation of an example of determining a cardiovascular parameter of a user using a universal cardiovascular manifold.

In a second specific example, the method includes: generating the universal manifold from population calibration data, determining a set of offsets for an individual manifold based on an individual's calibration data, determining a change in fiducial values for the individual, determining a cardiovascular parameter change based on the normalized universal manifold and the set of offsets, and calculating the cardiovascular parameter for the individual based on the cardiovascular parameter change. The universal manifold (e.g., reference relationship between one or more reference sets of fiducials and one or more reference cardiovascular parameters) is preferably normalized with respect to a baseline (e.g., a mean cardiovascular parameter and a mean set of fiducials and/or synthetic fiducial), but can be non-normalized and/or otherwise processed. The baseline can be determined using (e.g., averaging) measurements recorded during a rest state of one or more individuals, using a set of measurements recorded across a set of cardiovascular states for one or more individuals, and/or using measurements recorded during any other state. The set of offsets for the individual manifold (e.g., individual relationship) preferably includes one or more fiducial offsets (e.g., wherein the fiducial offset can be the average of the synthetic fiducials, the average values for each fiducial, etc.) and/or a cardiovascular parameter offset (e.g., the average of the cardiovascular parameters). The set of offsets can be determined based on a single calibration datapoint (e.g., while the individual is at rest) and/or multiple calibration datapoints. A change in fiducial values for the individual can be determined based on a PG dataset (e.g., a non-calibration dataset), or otherwise determined. The change can be relative to the fiducial offset and/or relative to another fiducial reference. The corresponding cardiovascular parameter change can be determined based on the (normalized) universal manifold prescribing a relationship between changes in fiducials (e.g., individual fiducials, synthetic fiducials, etc.) and changes in the cardiovascular parameter. The relationship can be a fiducial transformation (e.g., as previously described for a universal cardiovascular manifold), can be based on a fiducial transformation (e.g., the slope of a linear transformation between a synthetic fiducial and cardiovascular parameter), can be a relationship (e.g., a 1:1 mapping) between fiducials (e.g., individual fiducials and/or fiducial sets) and cardiovascular parameter measurements (e.g., individual measurements and/or sets of measurements; measured for one or more individuals), and/or can be otherwise defined. The cardiovascular parameter for the individual can be calculated by summing: the cardiovascular parameter change, the cardiovascular parameter offset, and/or a cardiovascular parameter reference (e.g., a cardiovascular parameter corresponding to the fiducial reference). An example is shown in FIG. 21. Additionally or alternatively, the individual's cardiovascular parameter value can be determined by calculating a universal fiducial value corresponding to the individual's fiducial value (e.g., based on the fiducial change and the fiducial offset), and identifying the universal cardiovascular parameter value on the universal manifold corresponding to the universal fiducial value. The universal cardiovascular parameter value can optionally be corrected by the individual's cardiovascular parameter offset. However, the cardiovascular parameter can be otherwise determined.

Embodiments of determining cardiovascular parameters can include determining a cardiovascular manifold for the individual. For example, an individual's cardiovascular manifold can correspond to a surface relating the individual's heart function, nervous system, and vessel changes. In a specific example, a cardiovascular manifold can map fiducial values to corresponding cardiovascular parameter values and nervous system parameter values (e.g., parasympathetic tone, sympathetic tone, etc.). However, the cardiovascular manifold can additionally or alternatively depend on the individual's endocrine system, immune system, digestive system, renal system, and/or any suitable systems of the body. The cardiovascular manifold can additionally or alternatively be a volume, a line, and/or otherwise be represented by any suitable shape. The individual's cardiovascular manifold is preferably substantially constant (e.g., slowly varies such as does not differ day-to-day, week-to-week, month-to-month, year-to-year, etc.) across the individual's lifespan. As such, an individual's cardiovascular manifold can be stored to be accessed at and used for analyzing the individual's cardiovascular parameters at a later time. However, an individual's cardiovascular manifold can be variable and/or change considerably (e.g., as a result of significant blood loss, as a side effect of medication, etc.) and/or have any other characteristic over time.

In some variants, the cardiovascular manifold can correspond to and/or be derived from the predetermined functional form (e.g., from the third variant of fiducial determination). However, the cardiovascular manifold can be otherwise related to and/or not related to the fiducials.

The cardiovascular manifold preferably corresponds to a hyperplane, but can additionally or alternatively correspond to a trigonometric manifold, a sigmoidal manifold, hypersurface, higher-order manifold, and/or be described by any suitable topological space.

For example, determining the cardiovascular manifold for the individual can include fitting each of a plurality of segments of a PG dataset (e.g., segmented dataset, processed dataset, subset of the dataset, etc.) to a plurality of gaussian functions such as, $$\hat{f}(t) = \sum_{i}^{N} p_{a_i}(\langle\varphi\rangle) e^{-\frac{(p_{b_i}(\langle\varphi\rangle)-t)^2}{p_{c_i}(\langle\varphi\rangle)}}$$

Where $\hat{f}(t)$ is the segment of the PG dataset, t is time, N is the total number of functions being fit, i is the index for each function of the fit; a, b, and c are fit parameters, and $p_{x_i}$ are functions of the cardiovascular phase $\langle\varphi\rangle$ where the fit parameters are constrained to values of $p_{x_i}$. The constraining functions can be the same or different for each fit parameter. The constraining functions are preferably continuously differentiable, but can be continuously differentiable over a predetermined time window and/or not be continuously differentiable. Examples of constraining functions include: constants, linear terms, polynomial functions, trigonometric functions, exponential functions, radical functions, rational functions, combinations thereof, and/or any suitable functions.

In a third variant, determining the cardiovascular parameters can include determining the cardiovascular parameters based on the supplemental data. For example, the fiducial transformation and/or manifold transformation can be modified based on the supplemental data (such as to account for a known bias or offset related to an individual's gender or race). Examples of supplemental dataset can include: characteristics of the individual (e.g., height, weight, age, gender, race, ethnicity, etc.), medication history of the individual (and/or the individual's family), activity level (e.g., recent activity, historical activity, etc.) of the individual, medical concerns, healthcare profession data (e.g., data from a healthcare professional of the individual), and/or any suitable supplemental dataset.

In a fourth variant, the cardiovascular parameters can be determined in more than one manner. For example, the cardiovascular parameters can be determined according to two or more of the above variants. In the fourth variant, the individual cardiovascular parameters can be the average cardiovascular parameter, the most probable cardiovascular parameters, selected based on voting, the most extreme cardiovascular parameter (e.g., highest, lowest, etc.), depend on previously determined cardiovascular parameters, and/or otherwise be selected.

Figure 18:
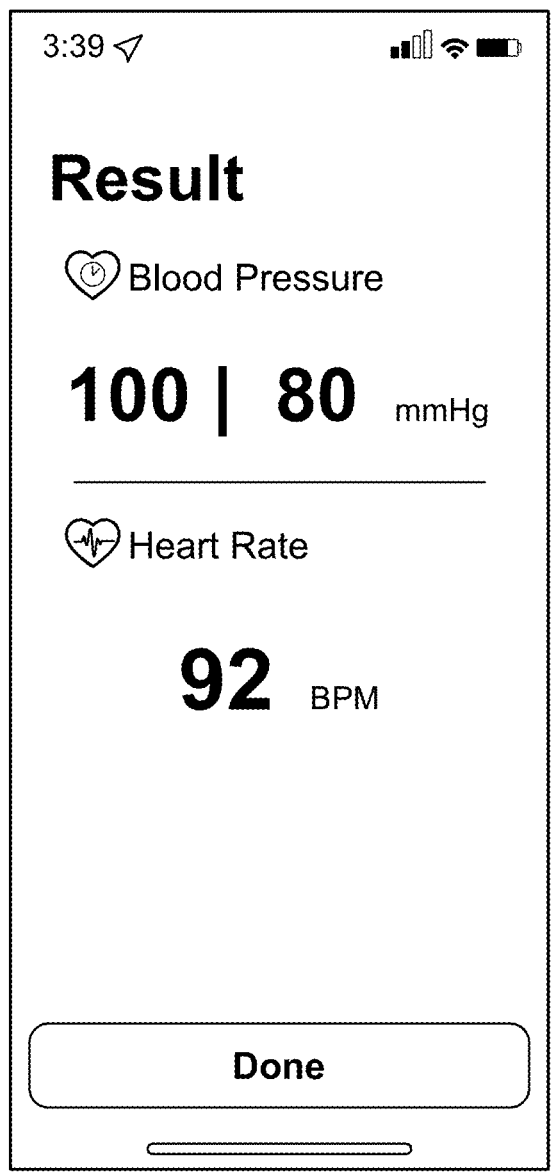
FIG. 18 depicts an illustrative example of displaying a cardiovascular parameter.

The cardiovascular parameter can optionally be: presented to the user (e.g., displayed at the user device; example shown in FIG. 18), provided to a care provider and/or guardian, used to determine a health assessment of the user (e.g., an assessment of cardiovascular disease such as hypertension, atherosclerosis, narrow of blood vessels, arterial damage, etc.), used to calibrate the cardiovascular parameter module (e.g., when compared to a cardiovascular parameter determined via a blood pressure cuff and/or any other system), and/or otherwise used. Additionally or alternatively, communication between the user and a healthcare provider can be initiated (e.g., automatically initiated) and/or otherwise facilitated based on the cardiovascular parameter, a treatment can be administered (e.g., automatically administered) based on the cardiovascular parameter, a treatment plan can be determined (e.g., automatically determined) based on the cardiovascular parameter, and/or the cardiovascular parameter can be otherwise used.

The cardiovascular parameter can be determined, in a first example, in a manner as disclosed in U.S. patent application Ser. No. 17/711,897 titled 'METHOD AND SYSTEM FOR DETERMINING CARDIOVASCULAR PARAMETERS' filed on 1 Apr. 2022 which is incorporated in its entirety by this reference. The cardiovascular parameter can be determined, in a second example, in a manner as disclosed in U.S. patent application Ser. No. 17/761,152 titled 'METHOD AND SYSTEM FOR DETERMINING CARDIOVASCULAR PARAMETERS' filed 16 Mar. 2022, which is incorporated in its entirety by this reference. The cardiovascular parameter can be determined, in a third example, in a manner as disclosed in U.S. patent application Ser. No. 17/588,080 titled 'METHOD AND SYSTEM FOR ACQUIRING DATA FOR ASSESSMENT OF CARDIOVASCULAR DISEASE' filed 28 Jan. 2022, which is incorporated in its entirety by this reference.

However, the cardiovascular parameter(s) can otherwise be determined.

Training a data quality module S500 functions to train one or more models in the data quality module (e.g., wherein the trained models can be implemented locally on the user device). S500 can be performed prior to: S100, S200, S300, and/or S400; and/or at any other time.

When more than one model is used (e.g., in a single data quality module, across multiple data quality modules, etc.), each model is preferably independently trained, but alternatively can be dependently trained. The same training data can be used to train different models and/or different training data can be used to train the models. For example, the same training data can be to train (e.g., independently train) a body region contact model and a placement model.

Training a data quality module can include: acquiring training data (e.g., via S100) with a set of training users under a first set of conditions (e.g., acceptable conditions, corresponding to one or more acceptable labels) and under a second set of conditions (e.g., unacceptable conditions, corresponding to one or more unacceptable labels), wherein the data quality module (e.g., a model in the data quality module) is trained to predict a label based on the training data (e.g., attributes extracted from the training data). The training data can optionally include overlapping time windows of data (e.g., to increase the amount of training data). The training data preferably includes data segments with the same size (e.g., same number of frames) as used in S200, but can alternatively be data of any size. The data segments preferably include the same type of data as that used in S200, but can additionally or alternatively include more or less data.

The labels are preferably binary (e.g., 'acceptable' or 'unacceptable'), but can alternatively be multiclass, a value (e.g., discrete, continuous, etc.), and/or any other label. In an example of multiclass labels, the labels can indicate a specific acceptable or unacceptable condition. In an illustrative example, the labels can be body region pose labels: 'too far left,' 'too far right,' 'too far up,' 'too far down,' and/or 'acceptable body region position.' In a second illustrative example the labels can be body region contact pressure labels: "pressure too low," "pressure too high," and/or "acceptable pressure." However, the labels can be otherwise configured. The labels can be: manually assigned, assigned based on the instructions given to the training user, determined using a secondary model, and/or otherwise determined.

In a first variant, the sets of conditions (e.g., acceptable and unacceptable conditions) are predetermined conditions. For example, acceptable and unacceptable conditions can be determined based on thresholds associated with the sensor. In a second variant, the sets of conditions can be empirically determined (e.g., during training, after training, during model testing, based on user testing, etc.). When more than one model is used, each model can be trained using the same or different sets of conditions. Acceptable and/or unacceptable conditions can optionally include multiple user devices (e.g., multiple makes and models), multiple environmental conditions (e.g., ambient light conditions), multiple user parameters, and/or any other parameters.

In an example of training a motion model, acceptable conditions can include: the user remaining seated and still; minimizing user device and/or user (e.g., body, arm, hand, and/or finger) movements during the measurement period (e.g., small device movement, device movement below a threshold motion, etc.); and/or any other conditions that facilitate high data quality. In specific examples, acceptable conditions can include: alternative user wrist poses (e.g., wherein the user device pose is based on the user wrist pose), slowly rotating and/or adjusting the user wrist, slight forearm movement and/or adjustment (e.g., up or down), slight user and/or user device bounce, slight user and/or user device movement due to breathing, talking and/or yelling, and/or any other acceptable pose and/or movement conditions. Unacceptable conditions can include: the user not remaining seated and/or still; the user and/or user device moving during the measurement period beyond a reasonable amount (e.g., beyond a threshold linear acceleration, angular acceleration, jerk, etc.); and/or any other condition that can lower data quality. In specific examples, unacceptable conditions can include: shaking the user device, rolling and/or rotating the user device, tapping the user device, lifting the body region on and off the sensor, swinging the user arm, raising and lowering the user arm, bouncing the user arm and/or hand, walking, running, squatting, spinning, jumping, going up and/or down stairs, getting up and/or sitting down, shaking (e.g., the user and/or user device), and/or any other unacceptable pose and/or movement conditions.

In an example of training a body region contact model, acceptable conditions can include: proper body region pose (position and/or orientation) relative to the sensor, proper contact pressure between the body region and the sensor, proper movement of the body region and/or user device (e.g., below a threshold motion), and/or any other conditions that facilitate high data quality. In a first specific example, acceptable conditions can include multiple body region orientations relative to the sensor (e.g., 0°, 45°, 90°, 135°, 180°, 225°, 270°, 315°, any number of degrees in the plane of the image sensor lens, etc.). In a second specific example, acceptable conditions can include a contact pressure 1 Oz-50 oz or any range or value therebetween (e.g., 2 Oz-15 Oz, 3 oz-10 oz, 4 oz-10 oz, the weight of the user device, etc.), but can alternatively include a contact pressure less than 1 oz or greater than 50 oz. Unacceptable conditions can include: improper body region pose relative to the sensor, improper contact pressure between the body region and the sensor, improper movement of the body region and/or user device (e.g., above a threshold motion), and/or any other conditions that can lower data quality. In a first specific example, unacceptable conditions include contact pressure too soft (e.g., hovering; below a first threshold contact pressure value) or too hard (e.g., squishing; above a second threshold contact pressure value). The first contact pressure threshold value can be between 1 oz-5 oz or any range or value therebetween, but can be less than 1 oz or greater than 5 oz. The second contact pressure threshold value can be between 5 oz-50 oz or any range or value therebetween, but can be less than 5 oz or greater than 50 oz. In a second specific example, the body region can be askew from covering the center of the sensor (e.g., too far in any direction, including left, right, up, down, any diagonal, etc.). The body region (e.g., the center of the body region) can be greater than a threshold value askew (in a given direction), wherein the threshold value askew can be between 1 mm-10 mm or any range or value therebetween (e.g., 1 mm, 2 mm, 3 mm, 4 mm, 5 mm, 6 mm, 7 mm, 8 mm, 9 mm, 10 mm, etc.), but can alternatively be less than 1 mm or greater than 10 mm. In other specific examples, unacceptable conditions include: body region movement (e.g., tapping finger on and off the image sensor; tapping the image sensor with the body region to mimic the appearance of heart beats in terms of light intensity changes and/or otherwise moving the finger; etc.), a foreign material or other obstruction between the body region and the sensor (e.g., Band-Aid™ or other bandage, paper, adhesive, clothing or other fabric, etc.), any other user body region (e.g., head, fingernail, etc.) on the sensor that is not a proper body region for the sensor (e.g., finger), a foreign material contacting the sensor instead of the body region (e.g., static and/or with movement; materials can include colored paper, a table, carpet, etc.), lighting (e.g., constant exposure to various lighting conditions), and/or any other unacceptable conditions.

In an example of training a placement model, acceptable conditions can be proper body region pose (position and/or orientation) relative to the sensor, proper contact pressure between the body region and the sensor, proper movement of the body region and/or user device (e.g., below a threshold motion), and/or any other conditions that facilitate high data quality. The acceptable conditions for placement model training are preferably the same as body region contact model and/or motion model acceptable conditions, but can alternatively be different than the body region contact model and/or motion model acceptable conditions. Unacceptable conditions can include: improper body region pose relative to the sensor, improper contact pressure between the body region and the sensor, improper movement of the body region and/or user device (e.g., above a threshold motion), and/or any other conditions that can lower low data quality. In a first specific example, the body region can be askew from covering the center of the sensor (i.e. too far in any direction, including left, right, up, down, any diagonal, etc.). The body region (e.g., the center of the body region) can be greater than a threshold value askew (in a given direction), wherein the threshold value askew can be between 1 mm-10 mm or any range or value therebetween (e.g., 1 mm, 2 mm, 3 mm, 4 mm, 5 mm, 6 mm, 7 mm, 8 mm, 9 mm, 10 mm, etc.), but can alternatively be less than 1 mm or greater than 10 mm. In a second specific example, unacceptable conditions include contact pressure too soft (e.g., hovering; below a first threshold contact pressure value) or too hard (e.g., squishing; above a second threshold contact pressure value). The first contact pressure threshold value can be between 1 oz-5 oz or any range or value therebetween, but can be less than 1 oz or greater than 5 oz. The second contact pressure threshold value can be between 5 oz-50 oz or any range or value therebetween, but can be less than 5 oz or greater than 50 oz. In other specific examples, unacceptable conditions can include: user (e.g., body region) and/or user device movement (e.g., not enough device movement for the motion model to detect; tapping and/or any other movement) no body region contact with the sensor (e.g., sensor exposed to open air, sensor contact with a variety of materials with and/or without movement, etc.) and/or any other unacceptable conditions (e.g., used for the motion model and/or the body region contact model).

The data quality module can optionally be trained using synthetic training data. For example, synthetic training data for a target user device (e.g., a target make and/or model) can be generated using models (e.g., physical models) of the target user device (e.g., based on non-synthetic training data for an initial user device and a physical model of the initial user device).

However, the data quality module and/or models therein can be otherwise trained.

Different subsystems and/or modules discussed above can be operated and controlled by the same or different entities. In the latter variants, different subsystems can communicate via: APIs (e.g., using API requests and responses, API keys, etc.), requests, and/or other communication channels.

Alternative embodiments implement the above methods and/or processing modules in non-transitory computer-readable media, storing computer-readable instructions that, when executed by a processing system, cause the processing system to perform the method(s) discussed herein. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A system, comprising:
 a processor configured to:
  receive a set of images of a body region of a user, the set of images sampled by an image sensor on a user device;
  using a first machine learning model, determine a contact data quality based on a total luminance, a total red chroma, and a total blue chroma of each image in the set of images;
  using a second machine learning model, determine a body region placement data quality based on summed luminance values across each row and across each column of each image in the set of images, wherein the second machine learning model is trained to predict body region placement data quality classifications based on sets of training images, wherein each set of training images is labeled with a body region placement data quality classification and corresponds to a time period window associated with multiple training images, wherein the time period windows are overlapping time period windows;

determine an overall data quality based on the contact data quality and the body region placement data quality;

generate a high quality plethysmogram (PG) dataset from the set of images when the overall data quality meets a criterion; and determine a cardiovascular parameter based on the high quality PG data.

2. The system of claim 1, wherein the high quality PG dataset is generated based on the total luminance of each of the set of images.

3. A method, comprising:
a) sampling a set of images of a body region of a user at an image sensor of a user device;
b) sampling motion data of the user device;
c) using a first trained machine learning model, determining a motion data quality based on the motion data;
d) using a second trained machine learning model, determining a contact data quality based on a first set of attributes extracted from the set of images;
e) using a third trained machine learning model, determining a body region placement data quality based on a second set of attributes extracted from the set of images, wherein the third trained machine learning model is trained to predict body region placement data quality classifications based on sets of training images, wherein each set of training images is labeled with a body region placement data quality classification and corresponds to a time period window associated with multiple training images, wherein the time period windows are overlapping time period windows;
f) determining an overall data quality associated with the set of images based on the motion data quality, the contact data quality, and the body region placement data quality;
g) contemporaneously with determining the overall data quality, generating a high quality plethysmogram (PG) dataset from the set of images based on the overall data quality; and
h) determining a cardiovascular parameter based on the high quality PG data.

4. The method of claim 3, wherein the contact data quality is associated with a presence of contact with the image sensor and is associated with a contact pressure between the body region and the image sensor.

5. The method of claim 3, wherein the body region placement data quality is associated with a position of the body region relative to the image sensor and is associated with a contact pressure between the body region and the image sensor.

6. The method of claim 3, wherein the first set of attributes comprises total luminance of each image in the set of images.

7. The method of claim 6, wherein the first set of attributes further comprises a total red chroma and a total blue chroma of each image in the set of images.

8. The method of claim 7, wherein the first set of attributes does not comprise green chroma.

9. The method of claim 3, wherein the second set of attributes comprises summed luminance values across each row and across each column of each image in the set of images.

10. The method of claim 3, wherein the body region placement data quality classifications comprise a classification corresponding to a contact pressure between a body region and an image sensor.

11. The method of claim 3, further comprising guiding the user based on the body region placement data quality to adjust a contact pressure between the body region and the image sensor.

12. The method of claim 3, wherein determining the cardiovascular parameter comprises:
determining a timing fit parameter of a fiducial model by fitting a first and second derivative of the fiducial model to the high quality PG dataset;
determining an amplitude fit parameter of the fiducial model by fitting a third derivative of the fiducial model to the high quality PG dataset; and
determining the cardiovascular parameter based on the timing fit parameter and the amplitude fit parameter.

13. The method of claim 12, wherein the fiducial model is one of a set of fiducial models, wherein determining the cardiovascular parameter further comprises:
determining a set of fiducials based on a timing fit parameter and an amplitude fit parameter for each of the set of fiducial models;
calculating a synthetic fiducial based on the set of fiducials, wherein the cardiovascular parameter is determined based on a linear relationship between the synthetic fiducial and the cardiovascular parameter.

14. The method of claim 3, wherein the high quality PG dataset is generated based on luminance values extracted from each of the set of images.

15. The method of claim 3, wherein generating the high quality PG dataset comprises:
when the overall data quality meets a criterion, extracting a first PG dataset from the set of images;
iteratively performing steps a)-f) to determine a second overall data quality associated with a second set of images;
when the second overall data quality meets the criterion:
extracting a second PG dataset from the second set of images; and
aggregating the first and second PG datasets; and
generating the high quality PG dataset based on the aggregated first and second PG datasets.

16. The method of claim 3, wherein determining the overall data quality comprises combining the motion data quality, the contact data quality, and the body region placement data quality.

17. The method of claim 16, wherein the motion data quality, the contact data quality, and the body region placement data quality are determined contemporaneously.

18. The method of claim 3, wherein the user device comprises a local computing system comprising the first, second, and third trained machine learning models.

19. The method of claim 3, wherein the cardiovascular parameter comprises at least one of a blood pressure or a heart rate.

* * * * *